US007682155B2

(12) United States Patent
Raven et al.

(10) Patent No.: US 7,682,155 B2
(45) Date of Patent: Mar. 23, 2010

(54) TRAINING DEVICE FOR AN AUTOMATIC INJECTOR

(75) Inventors: Sophie R. Raven, Swavesey (GB);
Grant Smetham, Nr Dorking (GB);
Matthew E. Young, Over (GB);
Cormac O'Prey, Bishops Stortford (GB); John G. Wilmot, Mount Airy, MD (US); Dominic C. Reber, Cambridge (GB)

(73) Assignee: Meridian Medical Technologies, Inc., Columbia, MD (US)

( * ) Notice: Subject to any disclaimer, the term of this patent is extended or adjusted under 35 U.S.C. 154(b) by 811 days.

(21) Appl. No.: 11/592,387

(22) Filed: Nov. 2, 2006

(65) Prior Publication Data

US 2007/0111175 A1 May 17, 2007

Related U.S. Application Data

(60) Provisional application No. 60/733,885, filed on Nov. 3, 2005.

(51) Int. Cl.
*G09B 23/28* (2006.01)
(52) U.S. Cl. .................................................. 434/262
(58) Field of Classification Search ................. 434/262, 434/267, 268, 272; 604/134, 135, 192–196
See application file for complete search history.

(56) References Cited

U.S. PATENT DOCUMENTS

| 3,426,448 | A |  | 2/1969 | Sarnoff | |
|---|---|---|---|---|---|
| 3,722,108 | A | * | 3/1973 | Chase | 434/267 |
| 3,795,061 | A |  | 3/1974 | Sarnoff et al. | |
| 4,481,001 | A | * | 11/1984 | Graham et al. | 434/267 |
| 4,640,686 | A |  | 2/1987 | Dalling et al. | |
| 5,037,306 | A |  | 8/1991 | van Schoonhoven | |
| 5,071,353 | A |  | 12/1991 | van der Wal | |
| 5,167,641 | A | * | 12/1992 | Schmitz | 604/196 |
| 5,320,609 | A | * | 6/1994 | Haber et al. | 604/135 |
| 5,567,160 | A |  | 10/1996 | Massino | |
| 5,727,948 | A | * | 3/1998 | Jordan | 434/267 |
| 5,890,908 | A | * | 4/1999 | Lampotang et al. | 434/268 |
| 6,162,197 | A |  | 12/2000 | Mohammad | |
| 6,238,407 | B1 |  | 5/2001 | Wolf et al. | |
| 6,656,164 | B1 |  | 12/2003 | Smith | |
| 7,416,540 | B2 | * | 8/2008 | Edwards et al. | 604/144 |

* cited by examiner

*Primary Examiner*—Kurt Fernstrom
(74) *Attorney, Agent, or Firm*—Jones Day; Garry J. Tuma

(57) ABSTRACT

A resettable training device and method for training a user on the operation of an auto-injector for dispensing a medicament are provided. The user can operate the training device to simulate an auto-injector operation and then reset the training device to repeat the injector operation. The training device includes a housing, a cover member slidably received within the housing between a retracted operative position and an extended inoperative position, a spring member for biasing the cover member into the extended position, an actuation assembly that controls the movement of the cover member from the retracted position to the extended position in response to activation of the trainer by the user, a safety pin, and in some embodiments at least one releasable locking assembly to prevent movement of the cover member from the extended position to the retracted position.

30 Claims, 22 Drawing Sheets

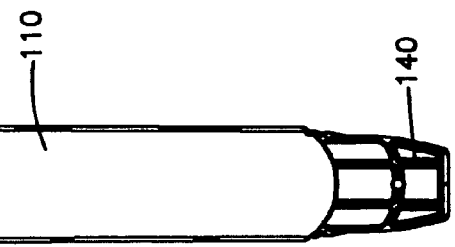
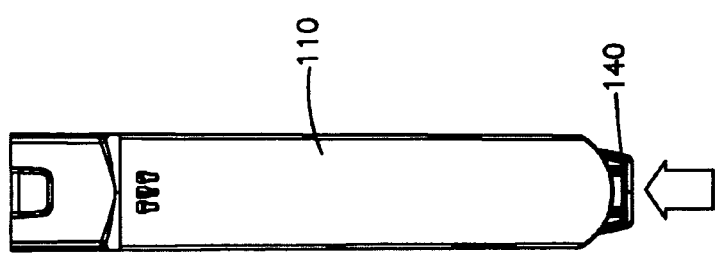
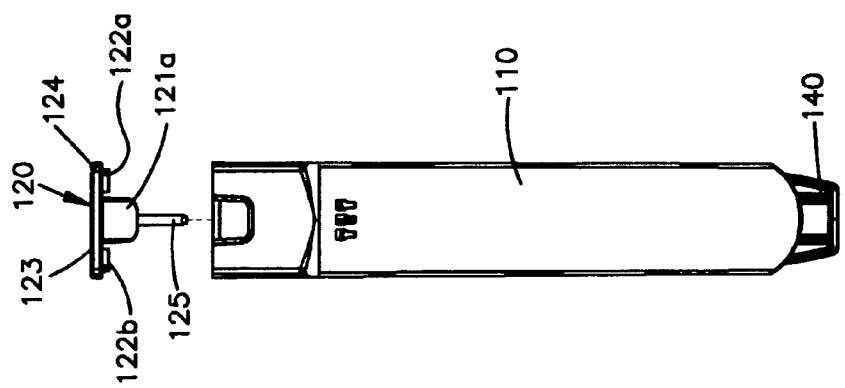
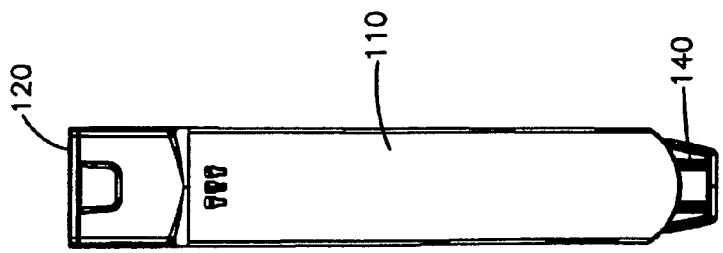

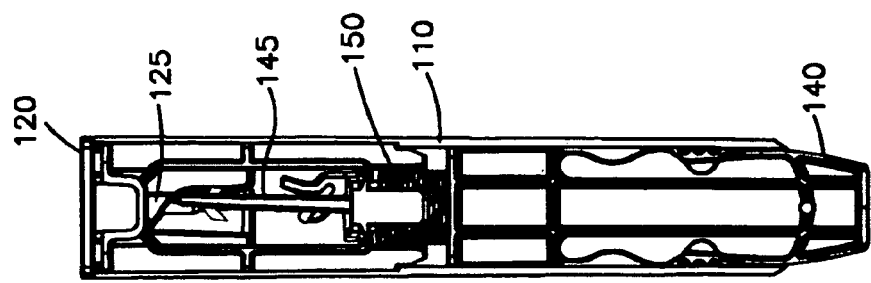
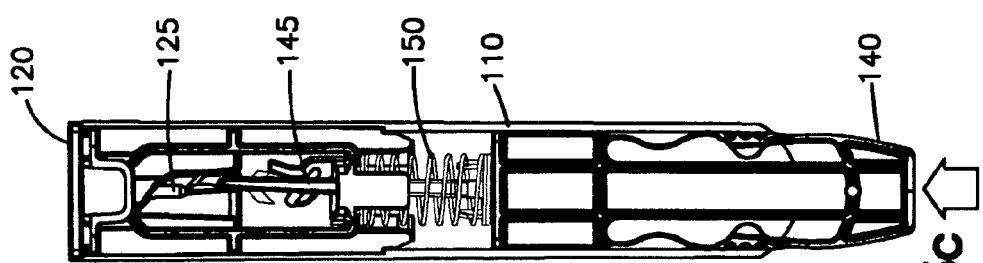
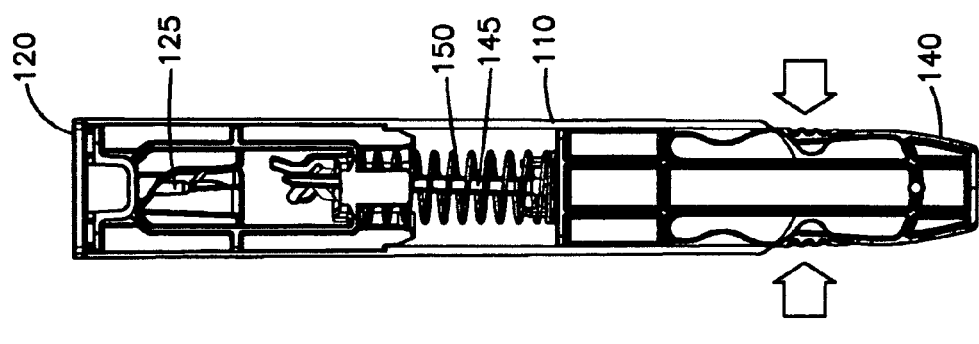
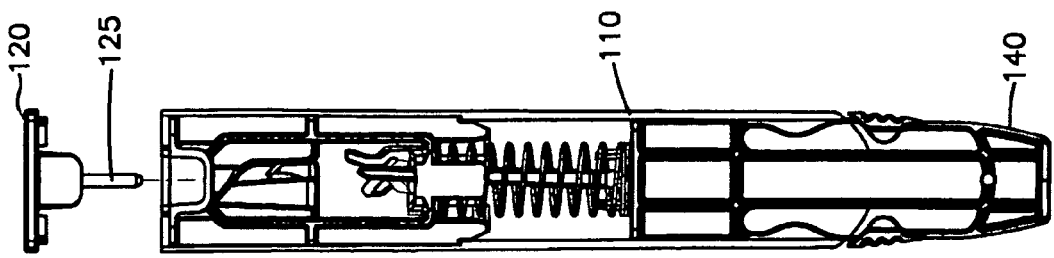

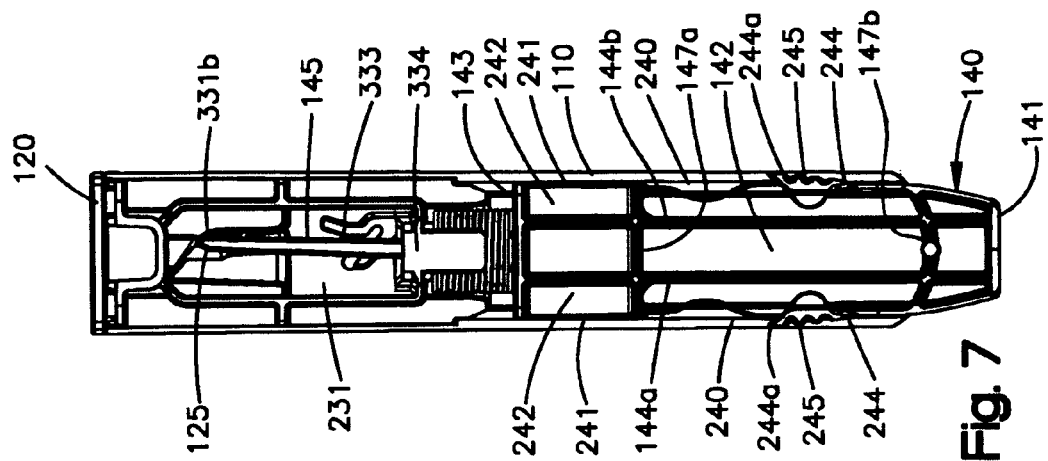
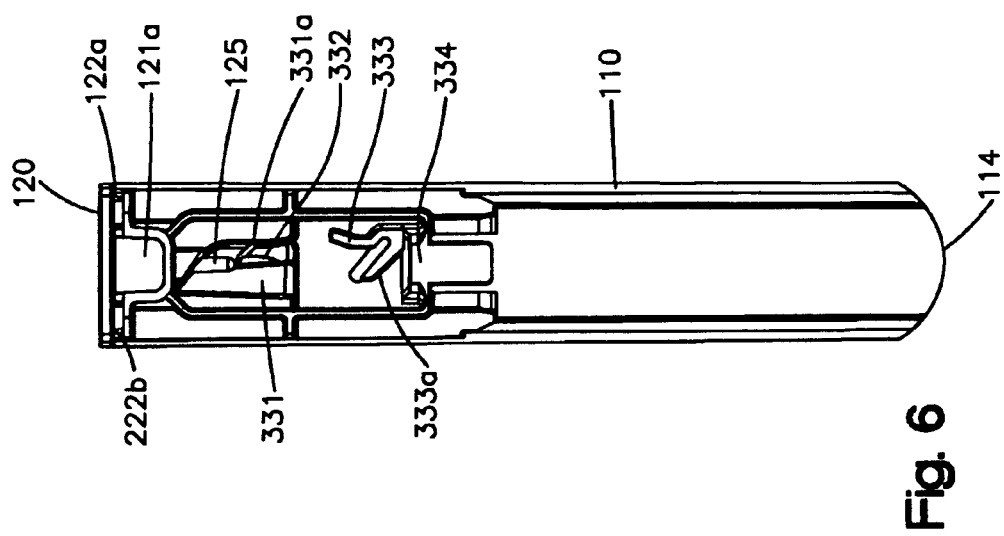

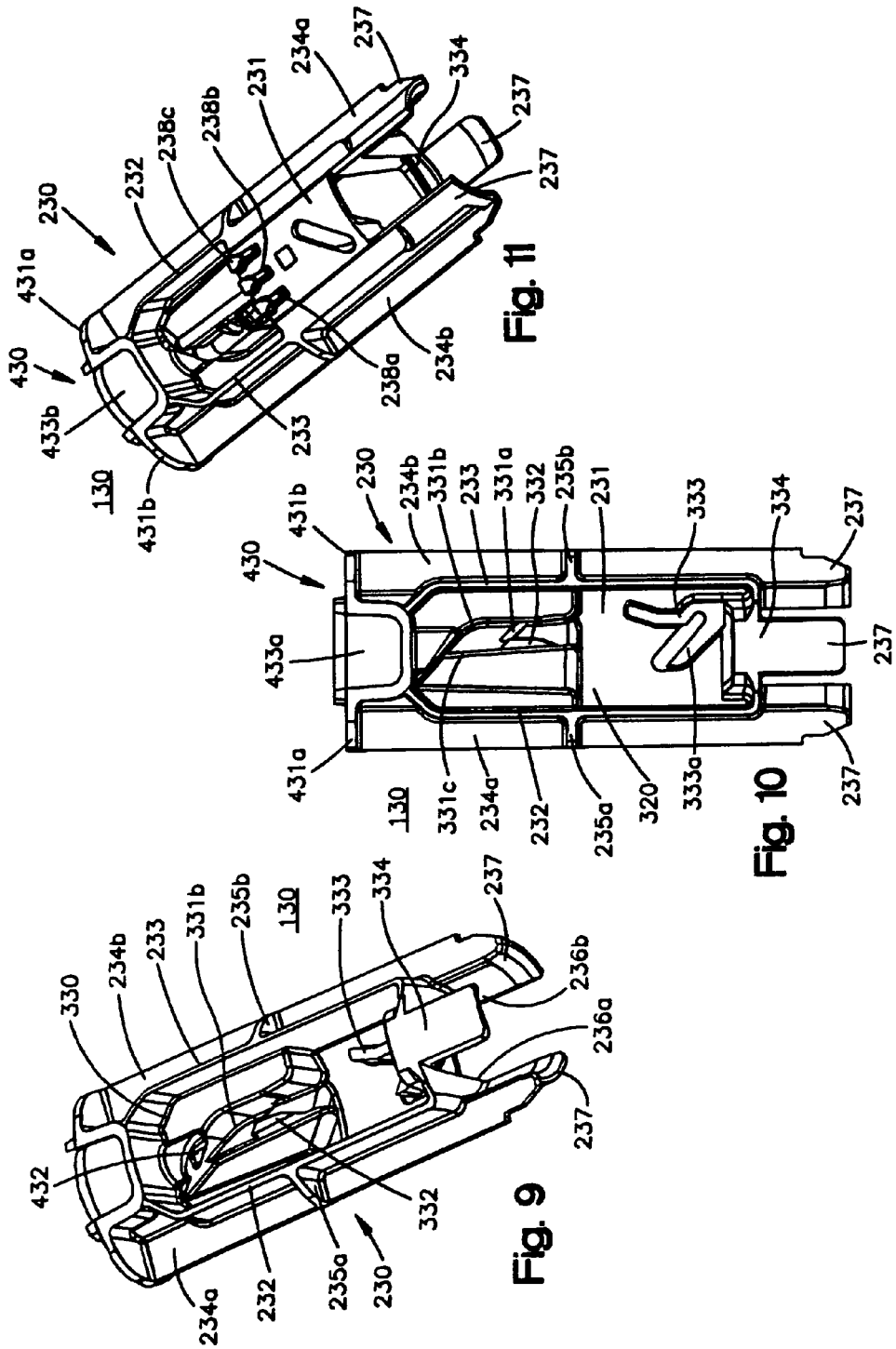

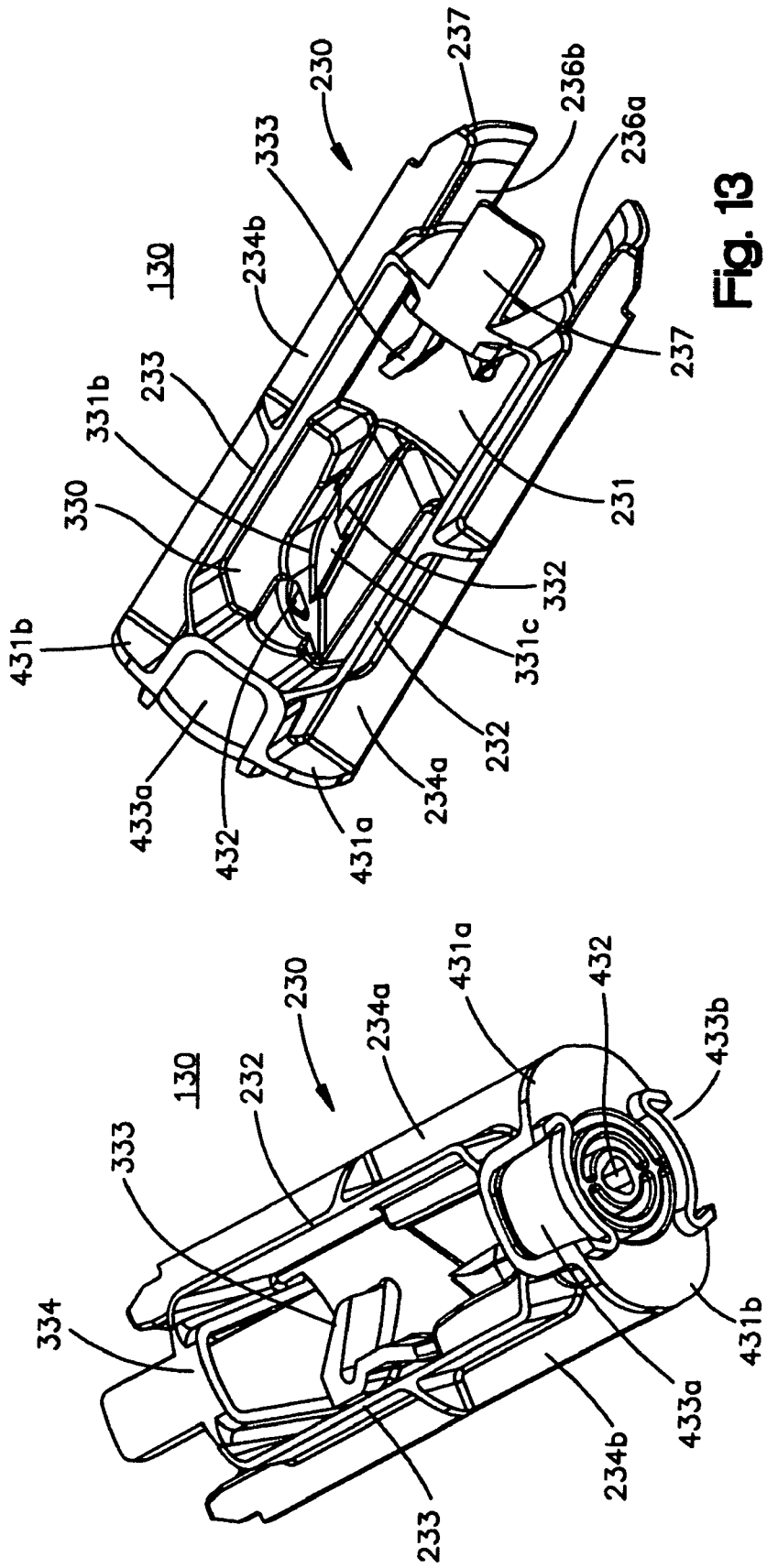

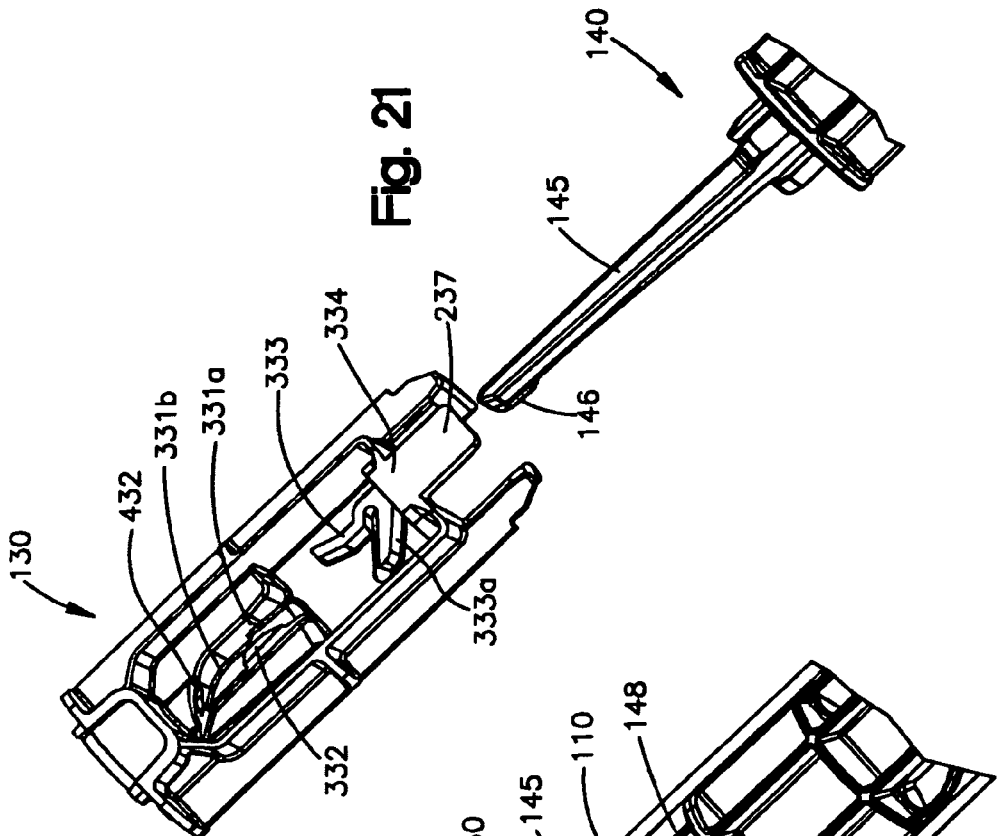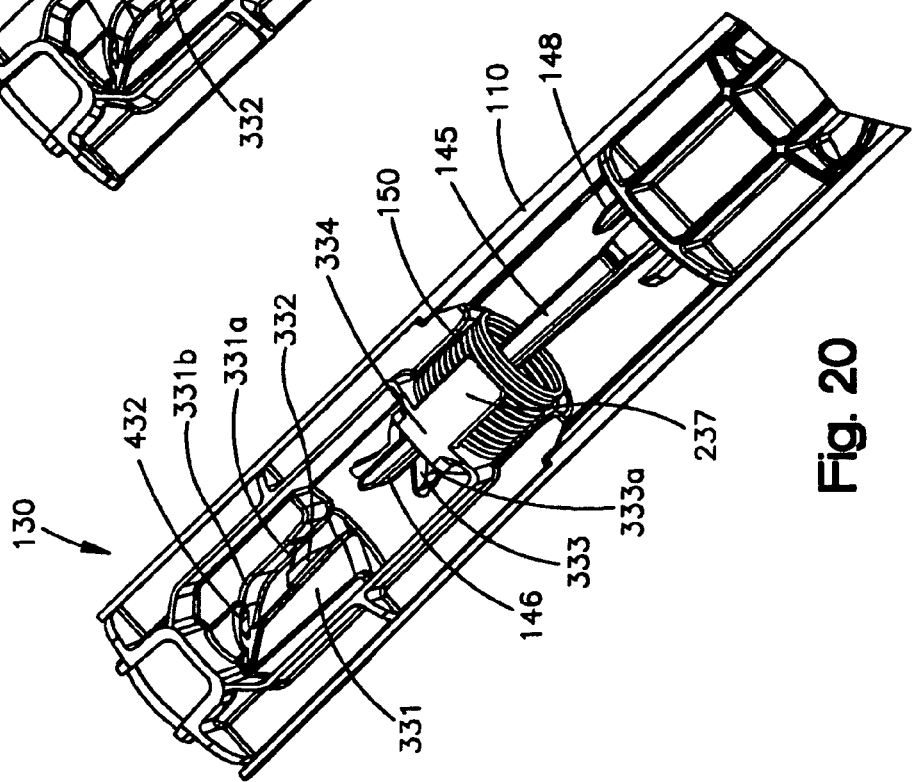

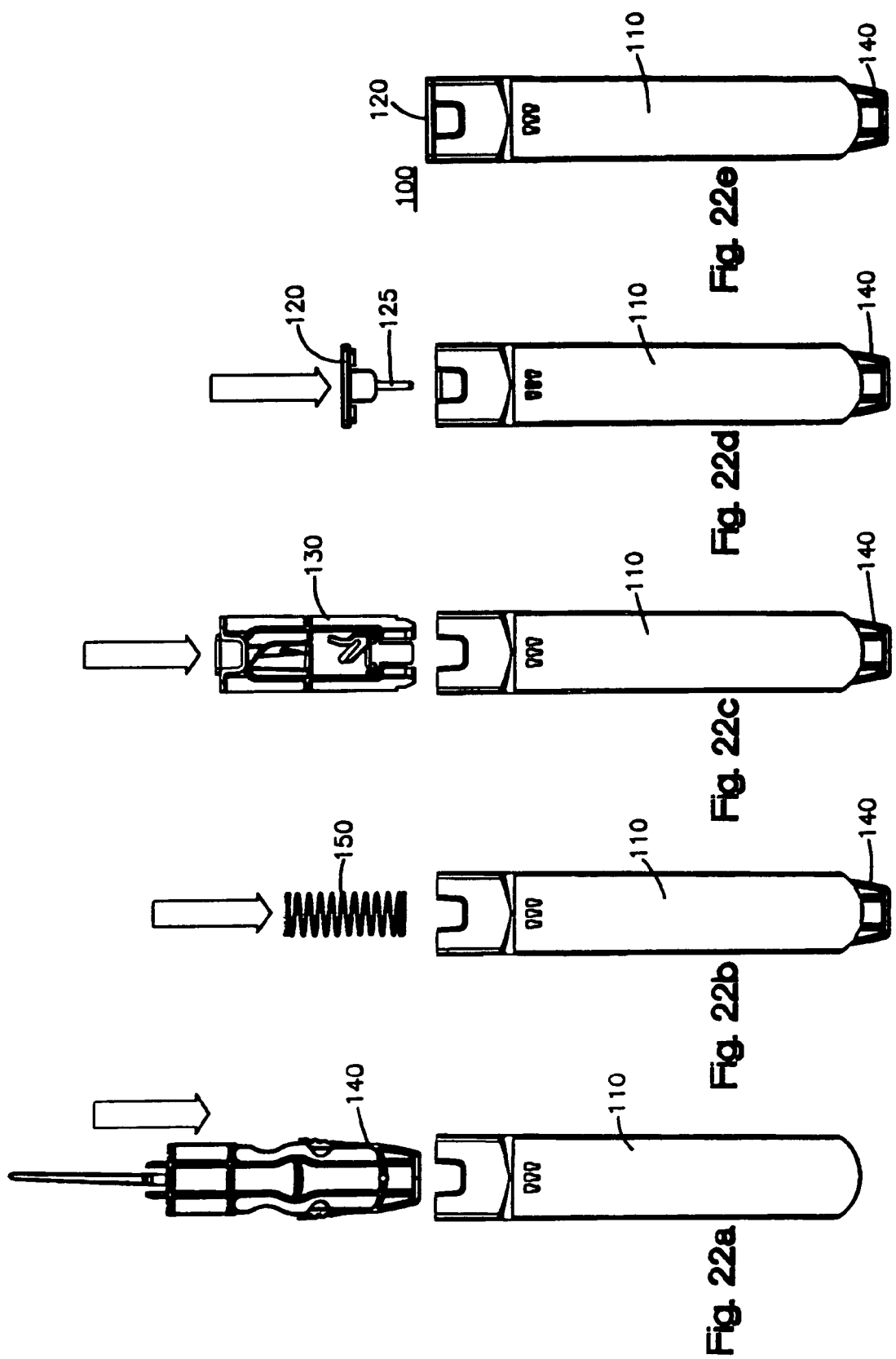

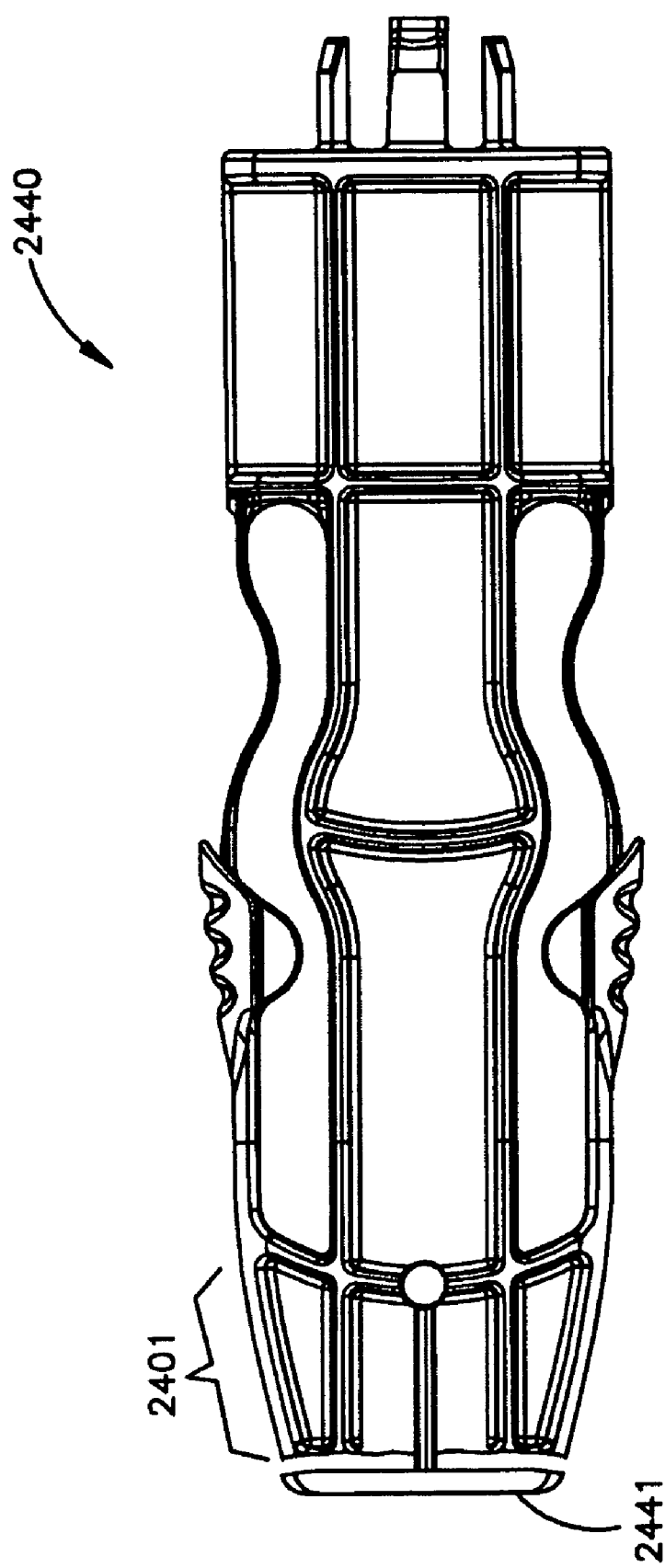

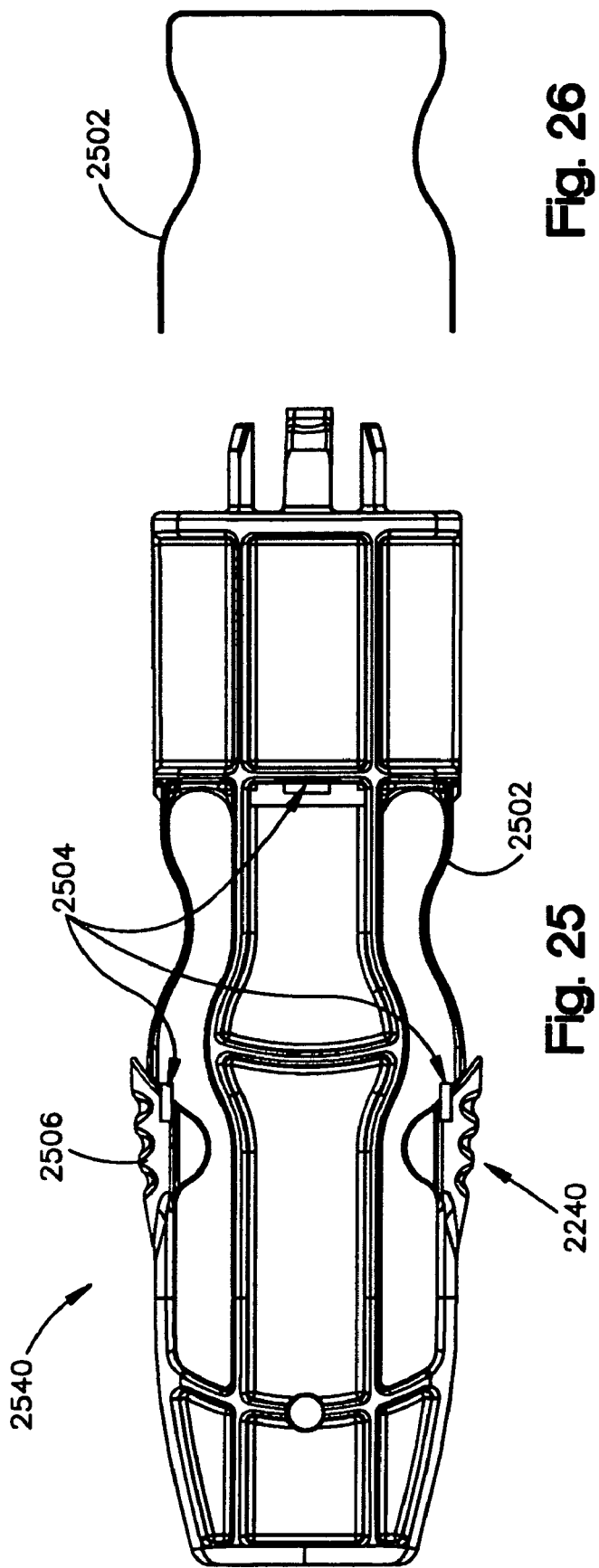

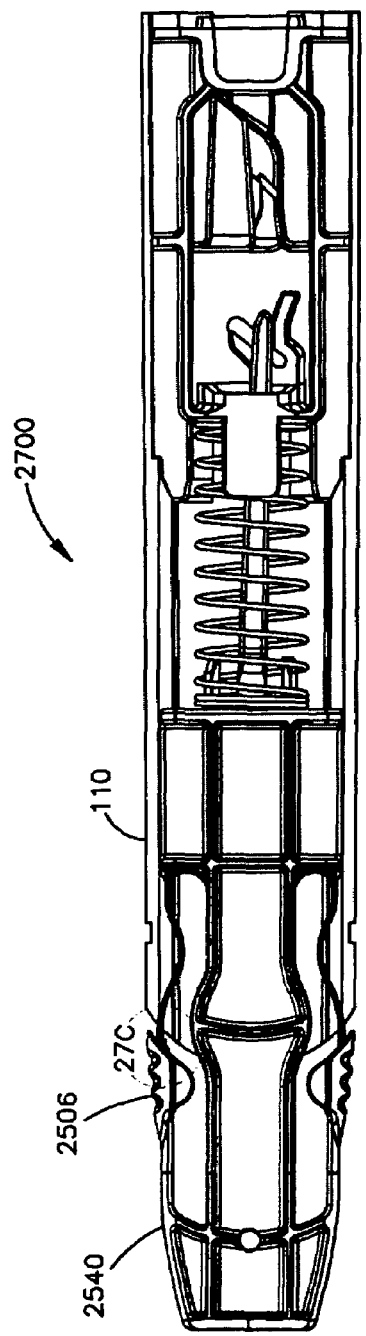
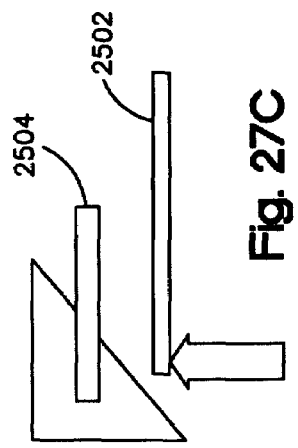
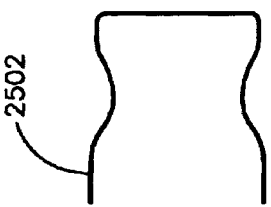

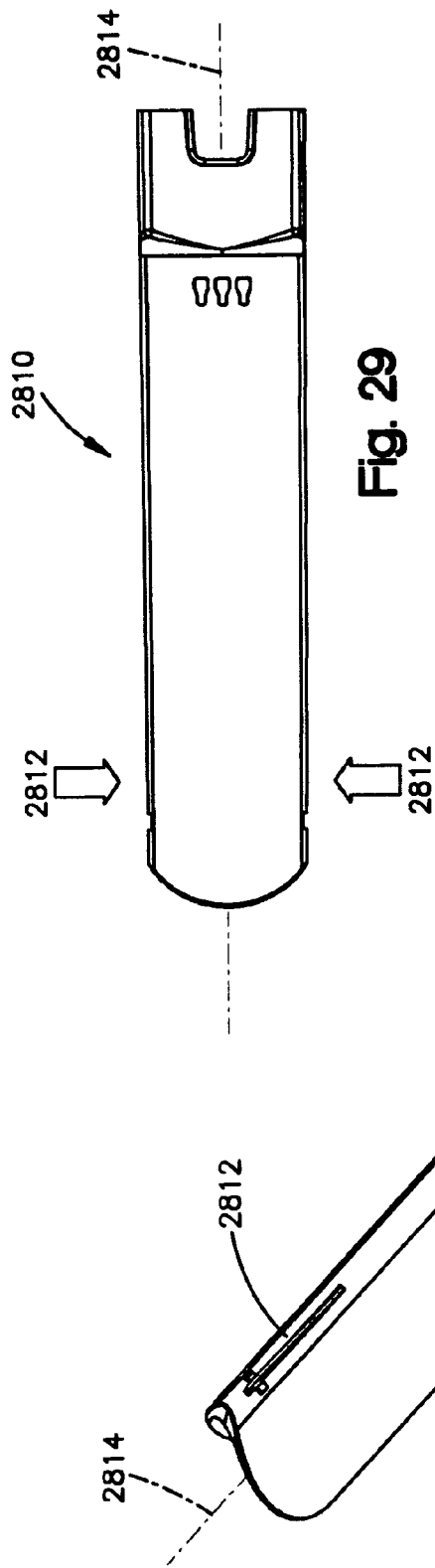

TRAINING DEVICE FOR AN AUTOMATIC INJECTOR

CROSS-REFERENCE TO RELATED APPLICATION

This claims the benefit of U.S. Provisional Patent Application No. 60/733,885, filed Nov. 3, 2005, the entire contents of which are expressly incorporated herein by reference thereto.

FIELD OF THE INVENTION

The invention relates to a training device for an automatic injector or auto-injector. Typically, an auto-injector is used for delivering medicament to an injection site. In particular, the invention is directed to a training device that simulates the process of using an auto-injector so that a user can become familiar with the process before actually administering a dose of medicament.

BACKGROUND OF THE INVENTION

An automatic injector is a well known device for enabling an individual to self-administer a dosage of a liquid medicament subcutaneously or intramuscularly, usually in an emergency situation. Automatic injectors are used, for example, to treat anaphylactic (severe allergic) reactions and to administer antidotes for certain poisons, such as chemical nerve agents and various drug compositions such as diazepan. An advantage of automatic injectors is that they contain a measured dosage of a liquid medicament in a sealed sterile condition capable of storage in such condition for an extensive period of non-use, during which period immediate injection of the stored dosage may be accomplished at any time under the most severe emergency conditions. For example, automatic injectors have heretofore been manufactured and sold containing nerve gas antidotes for use under chemical warfare conditions. In addition, units of this type have been proposed for use in administering antiarrhythmic medicaments under emergency conditions relating to heart attack medical situations. As another example, injection devices of this type have been marketed containing a dosage of epinephrine as an antidote for counteracting severe allergic reactions, such as from bee stings and the like.

A typical auto-injector has a housing, inside of which is a cartridge. The cartridge has one or more chambers containing medicament compositions or components thereof and is adapted to be attached to a needle assembly. The cartridge can hold either a pre-mixed liquid medicament or a solid medicament and a liquid that are to be mixed prior to injection. The housing carries an actuation assembly with a stored energy source such as, for example, a compressed spring. Activation of the actuation assembly causes a sequence of movements, whereby the needle extends from the auto-injector into the user such that the medicament compound is subsequently forced through the needle and into the user. If the auto-injector is of the type designed to carry plural components of the medicament composition in separate, sealed compartments, structure may be included that forces the components to mix when the actuation assembly is activated. After delivery of the dose of medicament into the injection site, the needle remains in an extended position.

It is important that the user of an auto-injector learn its proper operation and become comfortable with its use. Users should not hesitate to inject themselves, either from fear of using the device or for lack of knowledge in the proper use of the device, at the critical moment when injection is required. However, it is impractical for individuals to train with automatic injectors by repeatedly injecting themselves with a hypodermic needle. Thus, there is a need for a device that simulates the operation of an auto-injector whereby the user can practice and become familiar with the auto-injector's operation prior to dispensing any medicament. Training with such a device should prevent improper administering of the medicament, improper orienting of the auto-injector, and premature removal of the auto-injector prior to the full dispensing of the medicament.

Various training devices have been developed that enable a potential automatic injector user to become acquainted with its use. Examples of known training devices are disclosed in U.S. Pat. Nos. 3,426,448; 3,795,061; 4,640,686; 5,037,306; and 5,071,353.

While the aforementioned U.S. patents relating to training devices have been effective in simulating the action of the automatic injector, they are not very user-friendly in that they each require some awkward procedure to recock the training device for reuse. For example, in the aforementioned U.S. Pat. Nos. 5,071,353, and 3,795,061, an auxiliary recocking tool must be used. In U.S. Pat. Nos. 3,426,448 and 5,037,306, a manual manipulation of the device is required before the prod member (which is a blunt elongate member that outwardly projects from the forward end of the training device housing to simulate the outwardly projecting hypodermic needle) should itself be physically forced back into the body of the training device, for example, by being thrust against a surface. In U.S. Pat. No. 4,640,686, no prod member is provided, and the training device must be reset or recocked by placing a safety pin element on a horizontal surface and then moving the training device downwardly onto the safety pin element until an opening in the training device fully receives the pin.

From a utility standpoint, a training device should be made to closely simulate the action of an automatic injector. The training device should also be capable of repeated use and of being made ready for reuse very easily. U.S. Pat. Nos. 4,640,686 and 5,567,160, both of which are assigned to the assignee of the invention, disclose training devices that can be easily reused. These training devices, however, do not simulate the operation of an auto-injector having sharps protection (i.e., an auto-injector whereby a cover member is provided such that the user is not exposed to the used needle of the auto-injector). From a commercial standpoint, training devices should be made as inexpensively as possible. It is an object of the invention to provide an injection training device that is relatively inexpensive to manufacture and simpler to use than those training devices known in the prior art.

SUMMARY OF THE INVENTION

It is an aspect of the invention to provide a training device for training a user on the proper operation of an auto-injector for dispensing a medicament. The training device simulates the operation of an auto-injector. After training, the user should be comfortable with the operation of an auto-injector so as to properly and safely administer a dose of medicament.

In accordance with an aspect of the invention, the training device includes an elongated hollow housing. A cover member is slidably received within the housing. The cover member is slidable from a retracted position, whereby the cover member is substantially received within the housing prior to operation of the training device, to an extended position after operation of the training device. A spring member provides the biasing force for biasing the cover member into the extended position. An actuation assembly is operatively connected to the cover member. The actuation assembly controls the movement of the cover member such that the cover member can be held in a retracted position and moved from the retracted position to the extended position in response to activation of the trainer by the user. A safety pin is removably connected to the actuation assembly. When connected, the safety pin prevents the cover member from moving from the retracted position to the extended position.

The cover member preferably includes an elongated arm having at least one guide tooth formed thereon. The elongated arm extends into a central cavity in the actuation assembly, and the guide tooth is operatively connected to the actuation assembly.

The actuation assembly includes a guide track formed within the cavity. The guide tooth is constructed and arranged to travel along the guide track as the cover member moves from a substantially retracted position to the extended position. The actuation assembly further includes a guide adjacent the guide track for orienting the guide tooth within the guide track. The guide directs the movement of the guide tooth during both the training operation and the resetting operation. A retention bridge may be provided that contacts the elongated arm such that the guide tooth remains positioned within the guide track.

The guide track preferably includes a retention ledge formed therein. The retention ledge is constructed and arranged to limit movement of the cover member in a first direction; that is, the cover member does not move from the retracted position to the extended position in the first direction. The guide tooth contacts the ledge, which prevents the cover member from moving to the extended position in the first direction.

In accordance with an aspect of the invention, the safety pin is constructed and arranged to limit movement of the cover member in a second direction opposite the first direction; that is, the cover member does not move from the retracted position to the extended position when the safety pin is connected to the actuation assembly. The safety pin also serves to maintain the training device in an inoperative state. When the safety pin is removed, the cover member is capable of moving in the second direction in response to an application of force on the cover member so that the cover member can move to the extended position, which simulates the injection operation of the auto-injector.

In accordance with another aspect of the invention, the guide track includes an actuation ledge formed therein. The actuation ledge is constructed and arranged such that the cover member travels from the retracted position to the extended position when at least one guide tooth travels over the actuation ledge. The cover member travels from the retracted position to the extended position under the bias of the spring assembly.

The actuation assembly may also include a retention assembly to limit further movement of the cover member once the cover member is in the extended position. The actuation assembly may further include a retention bridge for contacting the elongated arm such that the guide tooth remains positioned within the retention assembly.

In accordance with another aspect of the invention, the cover member preferably includes at least one locking assembly to prevent movement of the cover member from the extended position to the retracted position once the cover member is in the extended position. Each locking assembly includes a locking arm connected to the elongated body of the cover member. During a training operation, the locking arm flexes to a locked position in which a locking surface on a portion of the arm engages a portion of the housing to maintain the cover member in the extended position. The locking arms are constructed and arranged to be temporarily compressed to disengage the locking surface from the housing so the cover member can be moved from the extended position to the retracted position. The locking portion may include a stop to limit the compression of the locking arms.

It is another aspect of the invention to provide a resettable training device for training a user on the operation of an auto-injector for dispensing a medicament. The user can operate the training device to perform a training operation that simulates the operation of the auto-injector and reset the training device in order to repeat the training operation. The training operation can be repeatedly performed until the user becomes comfortable with the auto-injector's operation. The training device includes a housing and a cover member slidably received within the housing. The cover member is slidable from a retracted operative position, where the cover member is substantially received within the housing prior to operation of the training device, to an extended position after operation of the training device. The cover member is capable of being returned to the retracted operative position during a resetting operation. An actuation assembly is operatively connected to the cover member. The actuation assembly controls the movement of the cover member such that the cover member can move from the retracted position to the extended position in response to activation of the trainer by the user. A safety pin is removably connected to the actuation assembly. The safety pin prevents the cover member from moving from the retracted position to the extended position when the safety pin is connected to the actuation assembly. At the initiation of the training operation, the safety pin is disconnected from the actuation assembly. The safety pin is reconnected to the actuation assembly at the initiation of the resetting operation. Some embodiments of the invention include at least one releasable locking assembly to prevent movement of the cover member from the extended position to the retracted position when the cover member is in the extended position. The releasable locking assembly is constructed and arranged such that the cover member can be moved from the extended position to the retracted position during a resetting operation performed by the user, which resets the trainer to the retracted operative position.

It is another aspect of the invention to disclose a method of training a user with a training device to properly operate an auto-injector to dispense a dosage of medicament. The training device includes a housing, a cover member slidably received within the housing between a retracted position and an extended position, an actuation assembly operatively connected to the cover member to control the movement of the cover member from the retracted position to the extended position, and a safety pin removably connected to the actuation assembly. The method includes removing a safety pin from one end of the training device to place the training device in an operative state, operating the training device such that the cover member moves from the retracted position to the extended position (placing the training device in an inoperative state), replacing the safety pin, and resetting the training device for reuse.

Operating the training device includes pressing an end of the training device opposite the safety pin location against a predetermined surface of the user (e.g., a thigh). The user applies a sufficient force on the training device such that the cover member moves from the retracted position to a further retracted position. The training device generates a click sound when the cover member moves from the retracted position to a further retracted position, which provides an audible indication to the user of a simulated injection operation. The training device is then held against the predetermined surface for a predetermined amount of time (e.g., 10 seconds). The training device is then removed from the predetermined surface, whereby the cover member moves from the retracted position to the extended position. In some embodiments of the invention, the cover member is locked in the extended state, while in other embodiments, the cover member is not.

In those embodiments of the invention where the cover member is locked, the training device preferably includes at least one releasable locking assembly that prevents movement of the cover member from the extended position to the retracted position after operation of the training device. The resetting operation includes releasing the releasable locking assembly and applying a force to one end of the cover member to move the cover member from the extended position to the retracted position. The training device generates a click noise when the cover member is in the retracted position. The releasable locking assembly may include a locking arm connected to an elongated body on the cover member. The locking arm may include a locking portion having a locking surface, wherein the locking arm flexes to a locked position in which the locking surface engages a portion of the housing to maintain the cover member in the extended position. A compressive force is applied on the locking arm by the user so the cover member can be inserted into the housing.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIGS. 2(a)-2(d) are side views illustrating the operating sequence of the auto-injector trainer, which simulates the injection operation of an auto-injector;

FIGS. 5(a)-5(d) are cross-sectional side views of the auto-injector trainer of FIGS. 3(a)-3(d), respectively, illustrating the operating sequence of resetting the auto-injector trainer for reuse;

FIG. 6 is a cross-sectional side view illustrating the positioning of the trainer actuation assembly and safety pin within the outer body of the auto-injector trainer;

FIG. 7 is a cross-sectional side view of the auto-injector trainer illustrating the position of the needle cover arm within the actuation assembly prior to removal of the safety pin and with the needle cover retracted within the outer body;

FIG. 9 is a left rear perspective view of an embodiment of a trainer actuation assembly according to the invention;

FIG. 10 is a side view of the trainer actuation assembly of FIG. 9;

FIG. 11 is a left front perspective view of the trainer actuation assembly of FIG. 9;

FIG. 12 is a top rear perspective view of the trainer actuation assembly of FIG. 9;

FIG. 13 is a rear side perspective view of the trainer actuation assembly of FIG. 9;

FIG. 20 is a perspective view illustrating the position of the needle cover arm within the trainer actuation assembly when the needle cover is in an extended position;

FIG. 21 is a side perspective view illustrating the trainer actuation assembly and the needle cover arm;

FIGS. 22(a)-22(e) are side views illustrating the assembly of the auto-injector trainer according to the invention;

FIG. 24 is a cross-sectional view of an alternative embodiment of a needle cover according to the invention;

FIG. 25 is a cross-sectional view of another alternative embodiment of a needle cover according to the invention;

FIG. 26 is a side view of a spring for the alternative needle cover of FIG. 25;

FIG. 27A is a cross-sectional view of an auto-injector trainer with an alternative needle cover according to the invention, FIG. 27B shows the spring of the auto-injector trainer of FIG. 27A, and FIG. 27C shows an enlarged sectional view of a spring retention feature of the auto-injector trainer of FIG. 27A;

FIGS. 28 and 29 are perspective and side views, respectively, of an alternative embodiment of an outer body of the auto-injector trainer according to the invention;

DETAILED DESCRIPTION OF THE INVENTION

An auto-injector trainer 100 in accordance with the invention is shown in connection with FIGS. 1-23. The auto-injector trainer 100 is an educational tool to educate users on the proper orientation and operation of an auto-injector. The auto-injector trainer 100 simulates the operation of an auto-injector disclosed, for example, in U.S. Provisional Patent Application No. 60/599,054, entitled "Automatic Injector," which is incorporated herein by reference. Auto-injector trainer 100 simulates the operation of an auto-injector so a user can practice administering a medicament without actually dispensing the medicament. Unlike the auto-injector, trainer 100 contains no medicament or needle assembly. The trainer 100 has the same look and feel as an auto-injector so a user can become comfortable with the auto-injector. The auto-injector trainer 100 can be easily reset to allow a user to repeat the simulated injection operation until the user becomes comfortable with the operation. Additionally, the trainer 100 can be used to train multiple individuals on the proper operation of an auto-injector. As such, family members can also be educated on the proper operation of the auto-injector in the event a person is unable to self-administer the medicament. Furthermore, the trainer 100 may be used as a training aid in a hospital, clinic, or physician's office. The trainer 100 simulates an injection operation of an auto-injector without using a needle and charge of medicament.

Figure 1:
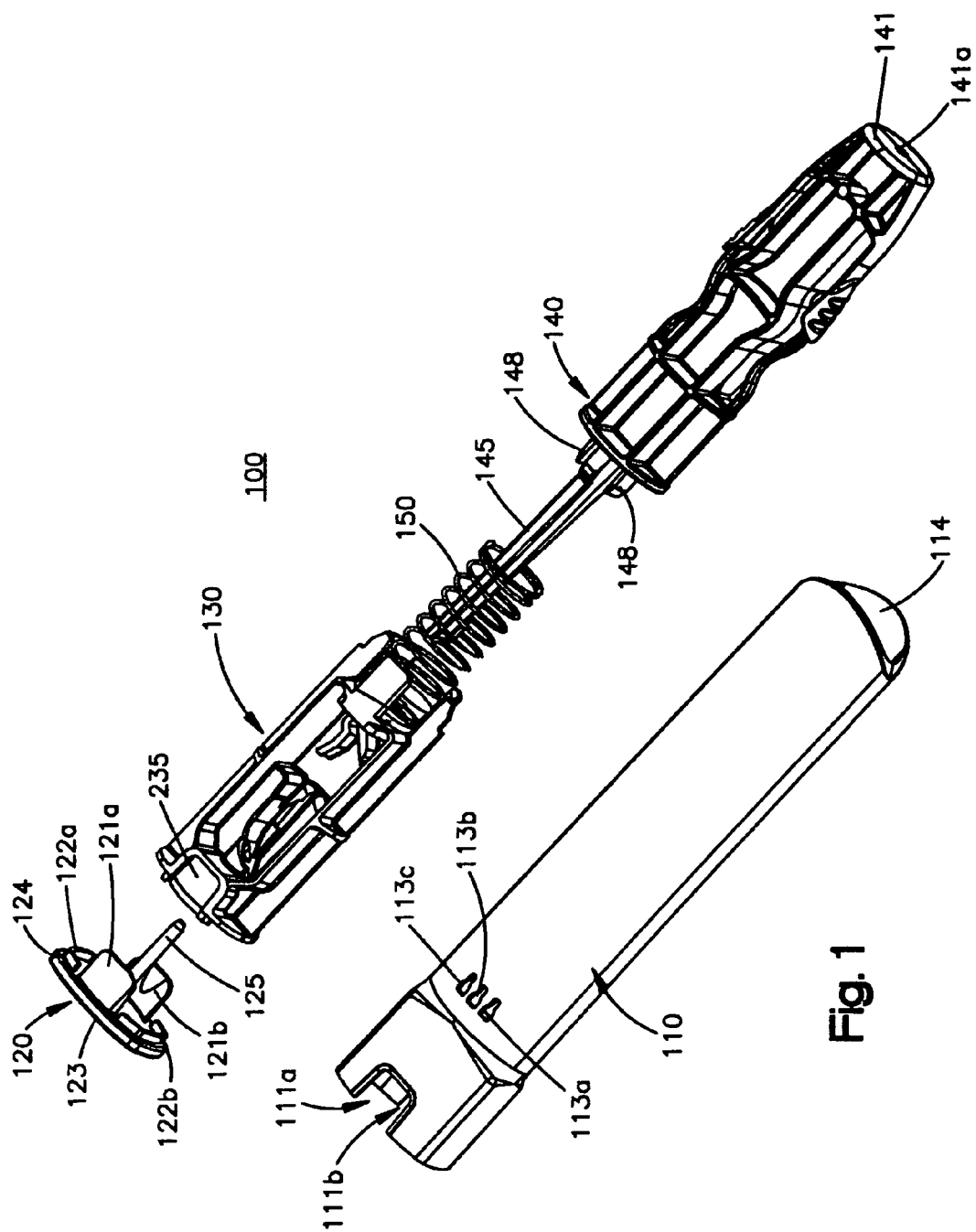
FIG. 1 is an exploded view of the components that form an embodiment of an auto-injector trainer according to the invention.

As shown in FIG. 1, the auto-injector trainer 100 includes an outer body or housing 110, a safety or release pin 120, a trainer actuation assembly 130, a trainer needle cover 140, and a spring assembly 150. Where possible, the auto-injector trainer 100 shares components with the auto-injector disclosed in U.S. Provisional Patent Application No. 60/599,054 (such as, e.g., the outer body 110, the spring assembly 150, and the safety pin 120).

The outer body 110 has a generally oval or elliptical shape, which is more ergonomically sized for easy grasping and use by a user or caregiver than a cylindrically-shaped body. The generally oval shape of the outer body 110 prevents the trainer 100 from inadvertently rolling or sliding off a flat surface. The shape of the outer body 110 corresponds to the shape of the outer body of an auto-injector. Furthermore, the oval shape provides a larger print surface for labeling the trainer 100 with instructions. The trainer 100 may include an instruction label 10, as shown, for example, in FIG. 23. The label 10 preferably provides instruction on the proper orientation and operation of the trainer 100, which simulates the operation of an auto-injector. Additionally, the label 10 should also include instructions for resetting the trainer 100. The outer body 110 is preferably formed from a synthetic material that can be easily molded. The outer body 110 has an opening 111 (see, e.g., FIG. 19) formed in one end that is sized to receive a safety pin 120. When in place, safety pin 120 prevents inadvertent use or activation of the trainer 100. The safety pin 120 is illustrated in FIGS. 1, 2(*b*), 4(*b*), 5(*a*), 6, 7, and 22(*d*).

Figure 19:
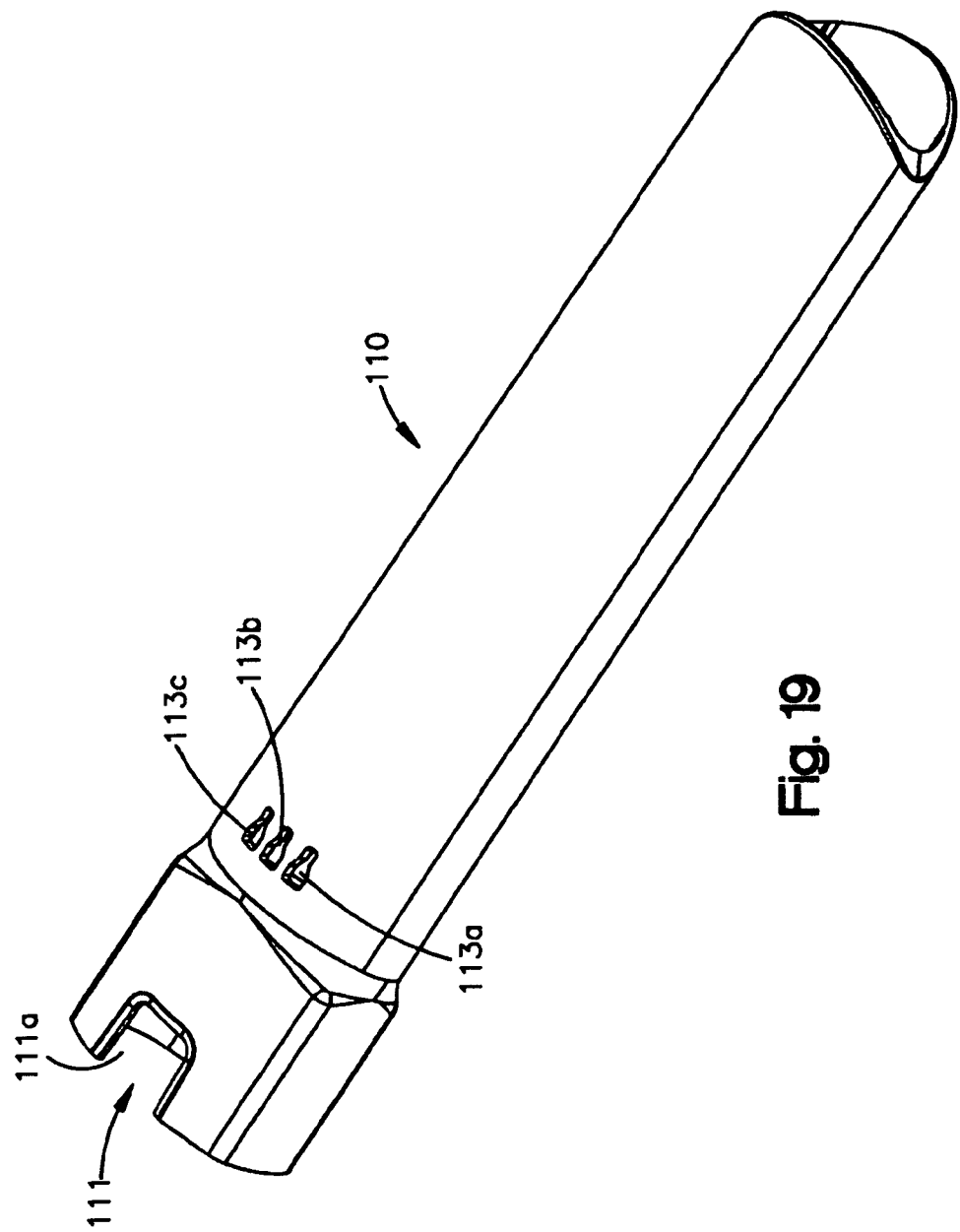
FIG. 19 is a left front perspective view of an embodiment of the outer body of the auto-injector trainer according to the invention.

The opening 11 includes side recesses 111*a* and 111*b*, which extend downwardly along opposing sides of the outer body 110, as shown in FIGS. 1 and 19. The recesses 111*a* and 111*b* are sized so that they may receive downwardly extending tabs 121*a* and 121*b* on safety pin 120. The tabs 121*a* and 121*b* prevent rotation of the safety pin 120 such that the user can easily recognize that the safety pin 120 is to be pulled rather than rotated when removing the safety pin 120 to actuate the auto-injector 100. The tabs 121*a* and 121*b* are primarily received in retention recesses 235 located on opposing sides of the actuation assembly 130, described in greater detail below. The recesses 111*a* and 111*b* provide access to the tabs 121 in the recesses 235. The tabs 121*a* and 121*b* are compression fit onto the actuation assembly 130 to prevent inadvertent removal. The safety pin 120 also includes downwardly projecting ribs 122*a* and 122*b*, which are adapted to be received on the top surface of the actuation assembly 130. The ribs 122*a* and 122*b* increase the stability and rigidity of the safety pin 120. The safety pin 120 includes an outwardly facing flat end 123 having a peripheral ledge 124. The peripheral ledge 124 permits grasping of the safety pin 120 by the user. The ledge 124 is sized to rest on the end surface of the outer body 110 adjacent opening 111. The safety pin 120 includes a downwardly extending pin 125, which extends into the trainer actuation assembly 130, as shown in FIGS. 4(*a*), 5(*b*), 5(*c*), 5(*d*), 6, and 7. When secured in place (i.e., prior to removal of the safety pin 120 and prior to actuation of the trainer 100, as shown in FIGS. 2(*a*), 4(*a*) and 7), the pin 125 prevents the end of the needle cover arm 145 from moving around a racetrack 331 in the trainer actuation assembly 130, which prevents actuation of the trainer 100. The end 123 has a shape corresponding to the oval/elliptical shape of the outer body 110.

As shown in FIGS. 4, 5, 7, 8 and 22(*b*), the outer body 110 is sized to receive therein the trainer actuation assembly 130, the trainer needle cover 140, and the spring assembly 150. A plurality of actuation assembly retention openings 113*a*, 113*b*, and 113*c* are formed on at least one side of the outer body 110. Projections or teeth 238*a*, 238*b*, 238*c* on the trainer actuation assembly 130, shown in FIG. 11, are snap fit into the openings 113. This snap fit prevents the removal of the trainer actuation assembly 130 from the outer body 110 once installed in the outer body 110. The actuation body 230 is not movable with respect to the outer body 110.

An opening 114 is formed in the outer body 110 on an end opposite the opening 111. The opening 114 is configured such that a portion of the trainer needle cover 140 extends therefrom. This end of the outer body 110 is intended to be oriented adjacent the surface of the user to be injected such that the end portion of the cover 140 is brought into contact with the injection surface.

The trainer actuation assembly 130 will now be described in greater detail in connection with FIGS. 6-14, 20 and 21. Unlike an actuation assembly in a traditional auto-injector, the actuation assembly 130 in trainer 100 does not provide an actuation force. Instead, the actuation assembly 130 controls the movement of the needle cover 140 in response to a spring force from the spring assembly 150 to simulate the actual operation of the auto-injector. The actuation assembly 130 includes a body 230 having a central cavity 330 formed by walls 231, 232, and 233. A pair of longitudinally extending ribs 234*a* and 234*b* extend from walls 232 and 233. A pair of peripheral ribs 235*a* and 235*b* also extend from walls 232 and 233. Rib 234*a* intersects rib 235*a*, and rib 234*b* intersects rib 235*b*. The ribs 234*a*, 234*b*, 235*a*, 235*b*; wall 231; and the edges of walls 232 and 233 contact the inner surface of the outer body 110 to prevent distortion of the outer body. Projections 238*a*, 238*b*, 238*c* extend from wall 231 and are sized to snap fit into openings 113*a*, 113*b*, 113*c* to secure the trainer actuation assembly 130 within the outer body 110. This construction permits the assembly 130 and body 110 to be secured together without an adhesive or other form of bonding.

A safety pin retention structure 430 (see, e.g., FIG. 10) is formed on one end of body 230. The retention structure 430 is integrally connected to walls 232, 233 and ribs 234*a* and 234*b*. The safety pin retention structure 430 forms the top end of the actuation assembly 130. The retention structure 430 includes a pair of peripheral wings 431*a*, 431*b*, which project radially outward like ribs 235*a* and 235*b*. The wings 431*a* and 431*b* form the top end of the assembly 130 and also serve to prevent distortion of the outer body 110. A safety pin retention hole 432 is provided to receive the downwardly extending pin 125 of the safety pin 120. As shown in FIGS. 6, 7, 9, 13 and 14, the hole 432 extends through the retention structure 430 and opens into the central cavity 330. When the pin 125 is located in hole 432, pin 125 extends into cavity 330.

Retention recesses 433*a* and 433*b* are formed on opposing sides of the retention structure 430 adjacent the top end surface. The recesses 433*a* and 433*b* are aligned with the side recesses 111*a* and 111*b* of the outer body 110 such that when the safety pin 120 is secured to the auto-injector 100, the tabs 121*a* and 121*b* are received in both recesses 433*a* and 433*b*. The recesses 433*a* and 433*b* are sized to apply a compressive force on tabs 121*a* and 121*b* to secure the safety pin 120 in place to prevent inadvertent removal.

The central cavity 330 of the trainer actuation assembly 130 will now be described in connection with FIGS. 6-14. The central cavity 330 includes a race track or guide track 331 formed on an interior surface of the actuation assembly 130.

Figure 14:
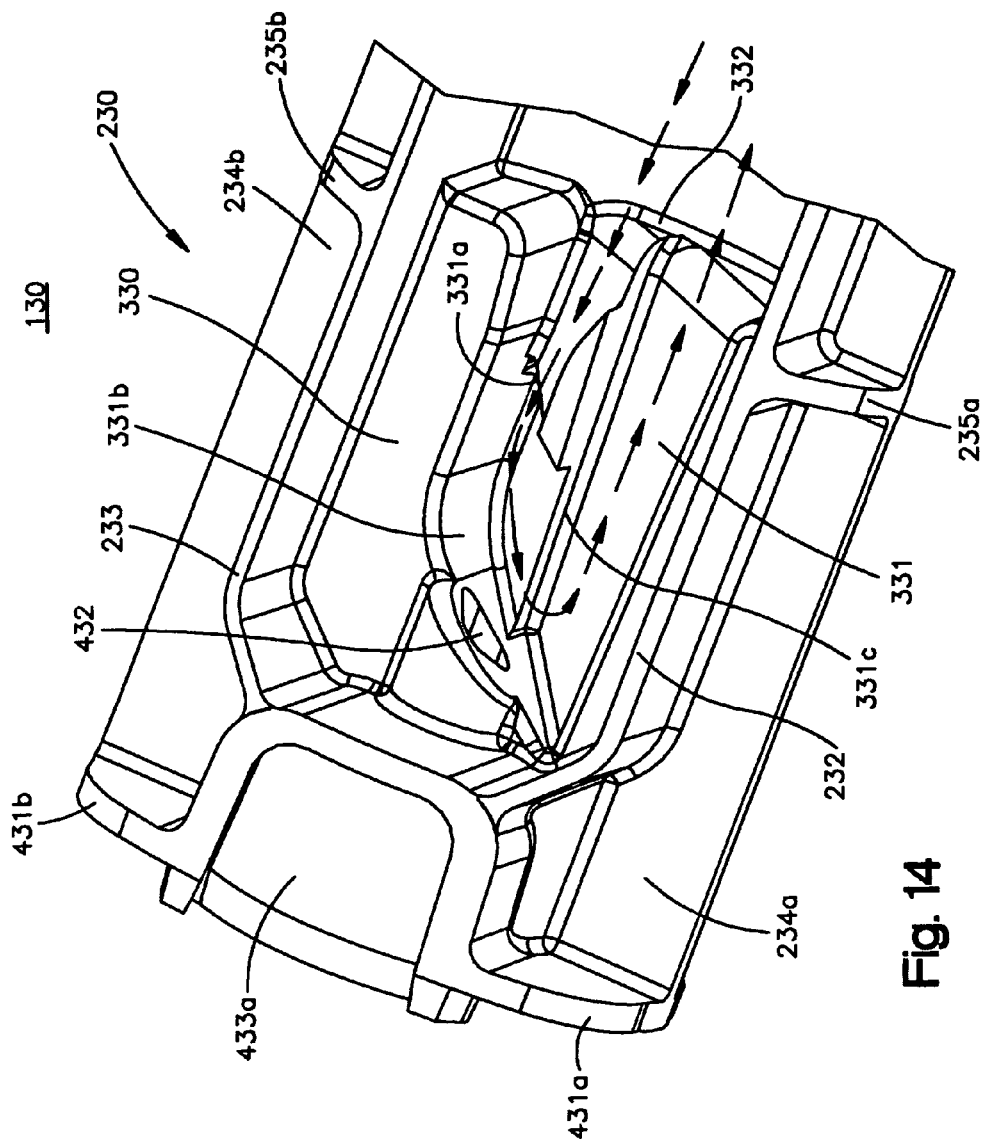
FIG. 14 is an enlarged schematic view of the central cavity of the trainer actuation assembly of FIG. 9, wherein the travel path of the needle cover arm is illustrated.

The race track or guide track 331 forms a guide path for the needle cover arm 145. The path of the needle cover arm guide tooth 146 is illustrated in FIG. 14. The central cavity 330 includes a guide detail 332, which is arranged within the race track 331 to ensure that the needle cover arm 145 and guide tooth 146 are properly oriented in the race track 331. The guide detail 332 directs the needle cover arm 145 and guide tooth 146 towards a retention ledge 331*a* formed in race track 331 as the needle cover 140 is pushed into the outer body 110. The retention ledge 331*a* retains the needle cover 140 in a retracted, ready for operation, position.

During operation of the trainer 100, the angled faces 331*b* and the connecting fillet surface control the force needed to direct the needle cover arm 145 through the race track 331. The angles of the faces 331*b* along with the spring assembly 150 ensure that the actuation force of the trainer 100 mimics the actuation force of an actual auto-injector. The race track 331 includes an activation ledge 331*c*. The activation ledge 331*c* provides a transition point within the race track 331. When the needle cover arm 145 drops off the activation ledge 331*c*, the needle cover arm passes along an opposite side of the guide detail 332. The needle cover arm 145 is free to travel along the race track such that the needle cover can extend to the fully extended position under the activation force of the spring assembly 150. When the needle cover arm 145 drops off activation ledge 331*c*, an audible "click" sound is generated that signals the start of the injection operation in an auto-injector.

The central cavity 330 includes a needle cover arm retention detail 333 (see, e.g., FIG. 10). The retention detail 333 is formed on an inner surface of wall 321 of body 230. The needle cover arm retention detail 333 retains the needle cover arm 145 such that the outward movement of the needle cover 140 is limited. Specifically, the guide tooth 146 is retained in the needle cover arm retention detail 333. The needle cover arm retention detail 333 includes an angled ramp 333*a* on an opposite side of detail 333. The ramp 333*a* assists in the assembly operation of the trainer 100, which is described in greater detail below. When the needle cover arm 145 is forced into the trainer actuation assembly 130, the guide tooth 146 tracks along ramp 333*a* until it is forced to pass retention detail 333. When a removal force is subsequently supplied to the needle cover 140, the guide tooth 146 is positioned in the retention detail 333.

The central cavity 330 includes a needle cover arm guide bridge 334. The needle cover arm bridge 334 holds the needle cover arm 145 in contact with the race track 331.

The actuation assembly body 230 includes a pair of ledges 236*a* and 236*b* formed on a lower portion of the body 230 (see, e.g., FIGS. 9 and 13). The ledges 236*a* and 236*b* provide a retention surface for the spring assembly 150. A plurality of stabilizing details 237 extend from the actuation assembly body 230 to provide support for the spring assembly 150.

The needle cover 140 will now be described in greater detail in connection with FIGS. 1, 7, 8 and 15-18. The needle cover 140 is intended to simulate the operation of the needle cover in an auto-injector. The needle cover 140 of the trainer 100 is not capable of receiving a needle or other components of a typical auto-injector. The needle cover 140 is slidably received within the outer body 110 such that it is moveable from a retracted position, shown in FIGS. 2(*a*) and 2(*b*), to an extended position, shown in FIGS. 2(*d*) and 3(*a*). Like the needle cover in an auto-injector, the needle cover 140 in the trainer 100 has a flat end surface 141 having an opening 141*a* formed therein. The opening 141*a* corresponds to an opening in the needle cover for an auto-injector where a needle would typically pass during an injection operation.

The needle cover 140 preferably has a one-piece molded construction. A central elongated body 142 extends from the end surface 141 to an opposing end surface 143. The end surface 143 has an oval shape, shown in FIG. 15, which corresponds to the oval shape of the outer body 110. A plurality of longitudinally extending reinforcing ribs 144*a* and 144*b* extend along the edges of body 142. Ribs 144*a* and 144*b* are located on both a front side and a rear side of body 142. In addition to reinforcing body 142, ribs 144*a* and 144*b* provide the needle cover 140 with an outer profile similar to the thickness profile of the needle cover of an auto-injector so that cover 140 can slide within outer body 110 in a similar fashion as the cover in an auto-injector. Peripheral ribs 147*a* and 147*b* also increase stability and serve to maintain the shape of the outer body 110.

Figure 18:
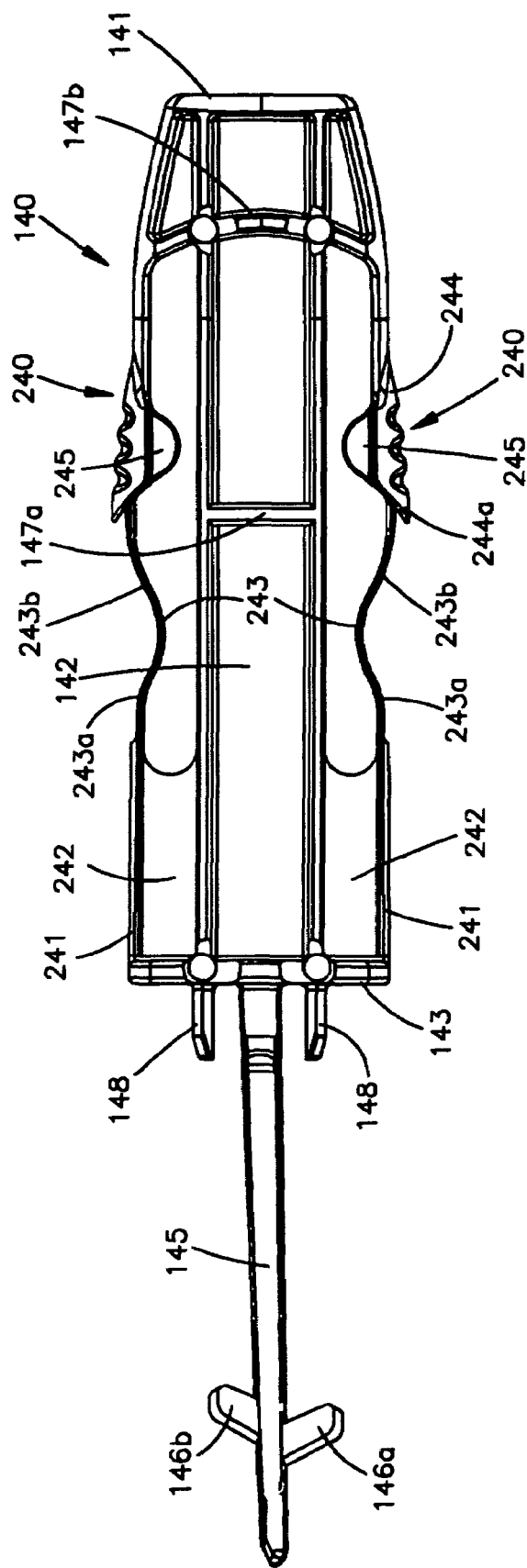
FIG. 18 is a side view of another embodiment of the needle cover according to the invention.

The needle cover arm 145 extends from the end surface 143 through the outer body 110 and into the trainer actuation assembly 130. At least one guide tooth 146 is located on a free end of the needle cover arm 145. The guide tooth 146 is configured to ride along race track 331 and engage the retention detail 333 at predetermined times. A variation of the guide tooth 146 is shown in FIG. 18 in which the guide tooth includes a pair of wings 146*a* and 146*b* extending from the sides of the needle cover arm 145 adjacent the end of the arm. Like the tooth 146, wings 146*a* and 146*b* are configured to travel along race track 331 and engage the detail 333 at predetermined times.

At least one spring guide projection 148 extends from the end surface 143. The guide projections function to position the spring assembly 150 such that the needle cover arm 145 extends through the center of the spring assembly 150, as shown in FIGS. 1, 4, 5, 7 and 8.

Figure 16:
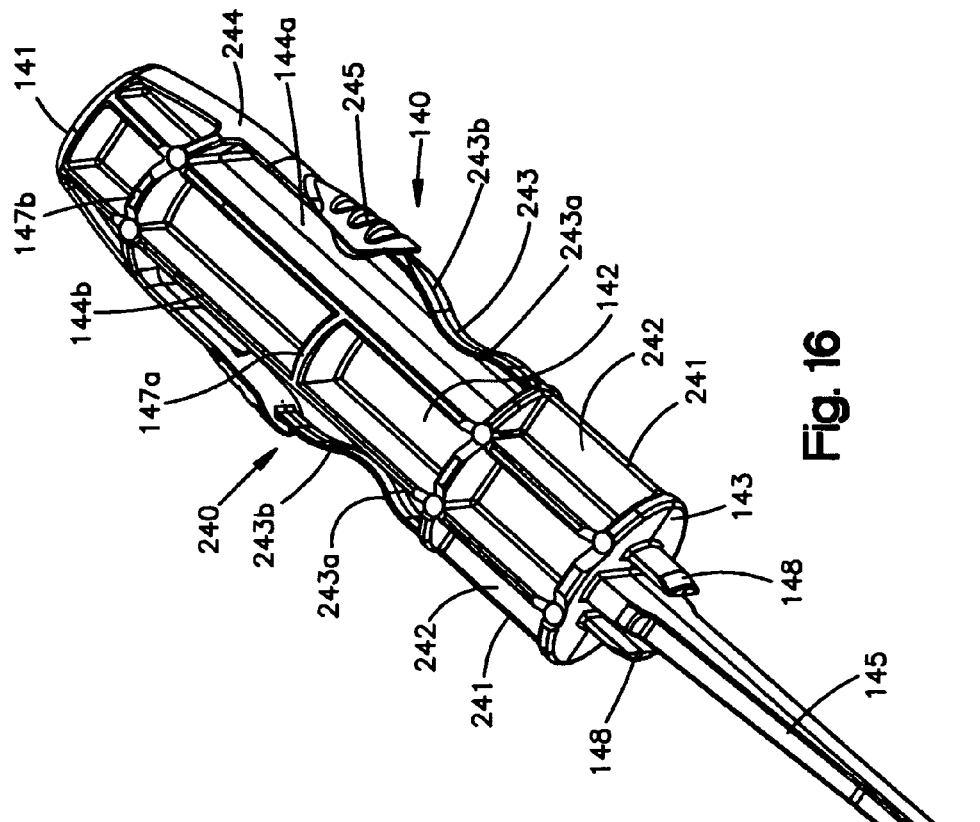
FIG. 16 is a schematic view of the needle cover.
Figure 15:
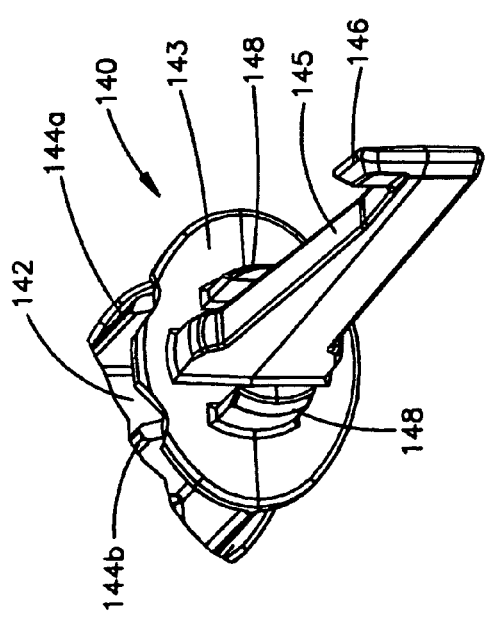
FIG. 15 is an enlarged schematic view of the needle cover arm.
Figure 17:
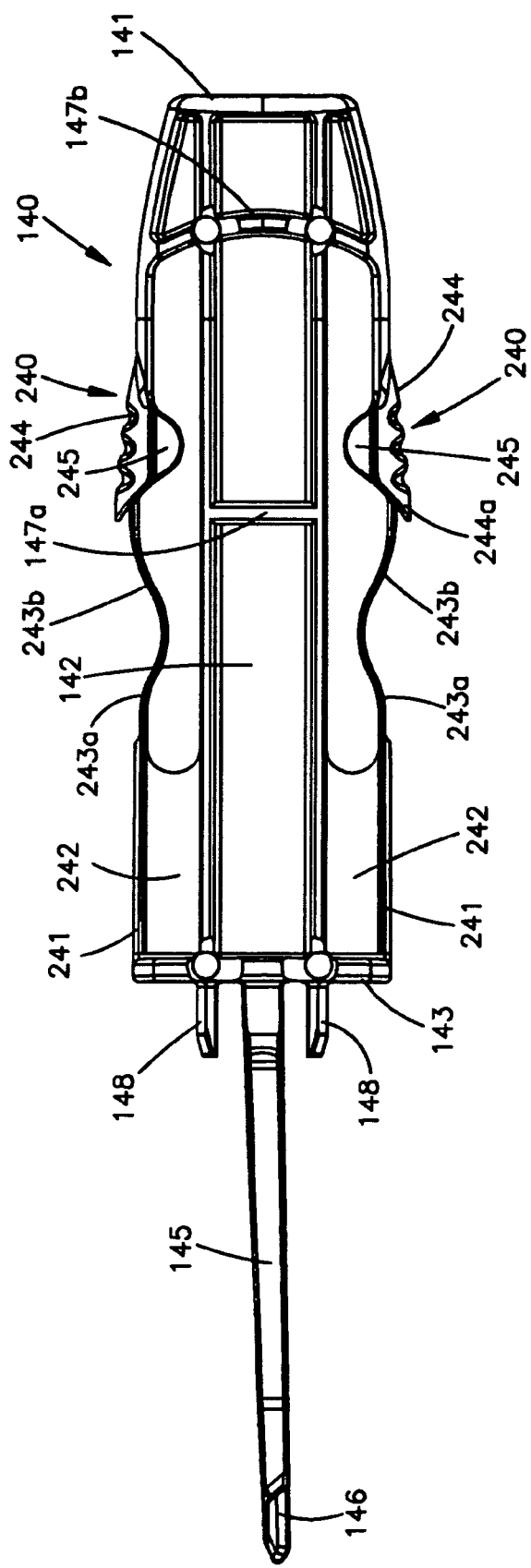
FIG. 17 is a side view of the needle cover of FIG. 16.

The needle cover 140 includes at least one needle cover locking arm 240. The needle cover locking arm 240 prevents the needle cover 140 from being pushed back into the outer body 110 of the trainer 100 after the trainer 100 has been removed from the injection surface after the injection operation. Each needle cover locking arm 240 includes an elongate portion 241 extending from the end surface 143. A reinforcing wing 242 is provided between a portion of the elongate portion 241 and the body 142, as shown in FIGS. 16 and 17. The reinforcing wing 242 stabilizes the elongate portion 241 to limit the inward flexing of portion 241 towards the body 142.

The locking arm 240 further includes a bend portion 243 having an inwardly directed portion 243*a* and an outwardly directed portion 243*b*. The bend portion 243 permits flexing of the locking arm 240 such that locking arm 240 can flex outwardly to engage the outer body 110 to maintain the cover 140 in an extended position, as shown in FIGS. 2(*d*), 4(*d*), 5(*a*) and 8. An elongated locking portion 244 extends between the bend portion 243 and the end surface 141. The locking portion 244 includes a beveled end surface 244*a*, which is shaped to contact the end surface of the outer body 110 when the needle cover 140 is in an extended position. In such an arrangement, the needle cover 140 cannot be retracted back into the outer body 110 without first compressing the locking arms 240.

When resetting the needle cover 140 (i.e., retracting it into the outer body 110), the user applies a compressive force on the elongated locking portion 244 (e.g., by squeezing the two locking portions 244 towards each other between the user's fingers) such that surface 244*a* clears the outer body 110 so the cover 140 can be pushed into the outer body 110 into the retracted position. A stop member 245 is positioned on an inner portion of locking portion 244 to limit the inward travel of the locking arm 240. The stop member 245 is arranged to contact the body 142 to prevent the locking arm 240 from being over compressed. This prevents damage to the locking arm 240. Additionally, the compressive forces are centered on the bend portion 243.

While under compression inside outer body 110, the needle cover locking arms 240 may over time undergo stress relaxation and may not return to their molded shape when deployed and thus fail to lock out needle cover 140 when in the extended position. FIGS. 24-29 show alternative embodiments of the needle cover locking arms that should reduce, if not eliminate, this possibility. FIG. 24 shows an alternative needle cover 2440 having an end surface 2441. Needle cover 2440 has a preferably "m" form or configuration at front end 2401 to increase the effective length of the locking arms. This reduces the strain on the locking arms, which in turn reduces stress relaxation.

FIGS. 25 and 27 show another embodiment of a needle cover. Alternative needle cover 2540 includes a preferably single-piece metal leaf spring 2502 (also shown in FIG. 26), which forms part of the needle cover locking arms 2240. Spring 2502 is pre-tensioned to move needle cover locking arms 2240 out against the retaining force from the stress relaxation. Needle cover 2540 preferably includes retention features 2504 to secure spring 2502 in position. As shown assembled in auto-injector trainer 2700 (FIG. 27), needle cover 2540 is visibly similar to needle cover 140. Spring 2502 is for the most part hidden in outer body 110. Note that the spring arms of spring 2502 should be free to move against the inside of the needle cover arm finger grips 2506. Spring 2502 may be assembled and retained in place after needle cover 2540 has been molded. Alternatively, single-piece spring 2501 can be snapped across the insides of finger grips 2506. In another embodiment, spring 2501 instead may be a pair of twin spring strips, one attached to each side of needle cover 2540.

FIGS. 28 and 29 show an alternative embodiment of an outer body that can be used with auto-injector trainer 2700 and needle cover 2540. Outer body 2810 preferably has cutouts 2812 sized and configured such that needle cover locking arms 2240 are not under any compression when in the reset (or operative) position. Cutouts 2812 may be formed by cutting into the sides of outer body 2810 along the major (longitudinal) axis 2814 and may be formed in a post-molding operation. Cutouts 2812 should be long enough to accommodate the length of finger grips 2506 and the activation stroke (which is from the retracted position to the extended position). Preferably, cutouts 2812 are slot-shaped to minimize the visible and tactile impact of the cutouts and, preferably, the finger grips are formed to match the profile of the slots. Also, label 10 (FIG. 23) should have a backing strip in the area surrounding the slots to prevent the label from sticking to the needle cover.

Needle covers 140, 2440, and 2540 may be made with Delrin 900P. Alternatively, higher molecular weight grades of Delrin (e.g., 500P/100P) are likely to improve the performance of the needle cover. Also, filled materials such as glass-filled grades of Delrin (having about 3× the stiffness of unfilled grades) may be used instead to form the needle covers. And as a further alternative, filled polymer materials may be used.

Figure 30:
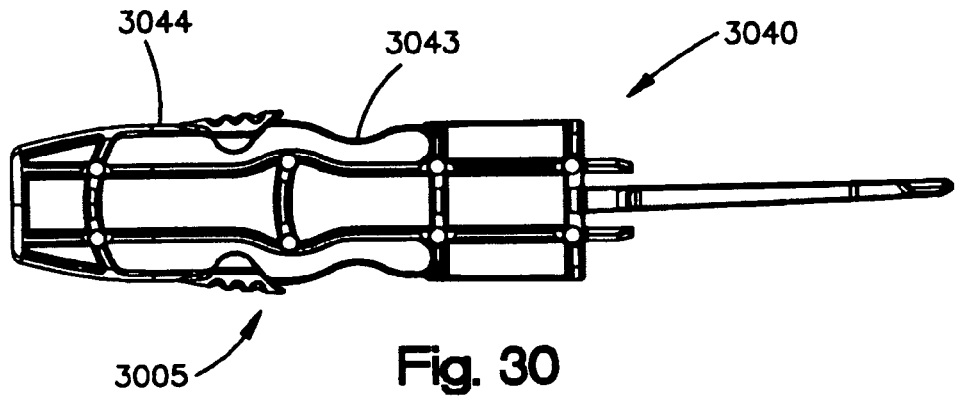
FIGS. 30 and 31 are cross-sectional views of alternative embodiments of non-locking needle covers according to the invention.
Figure 31:
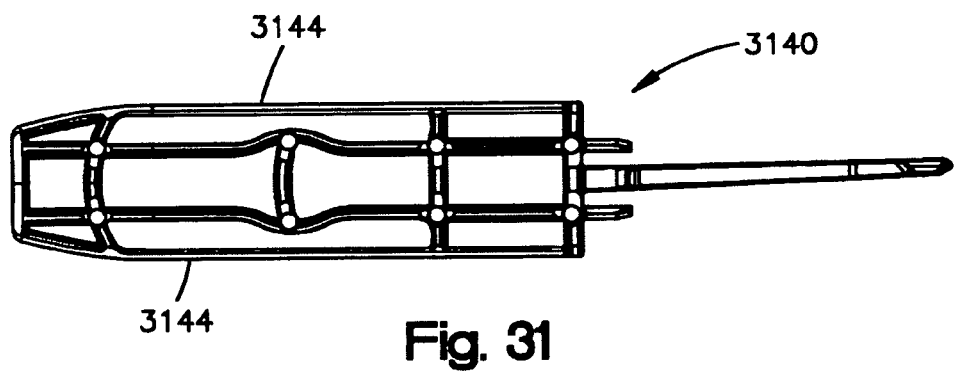
Figure 32:
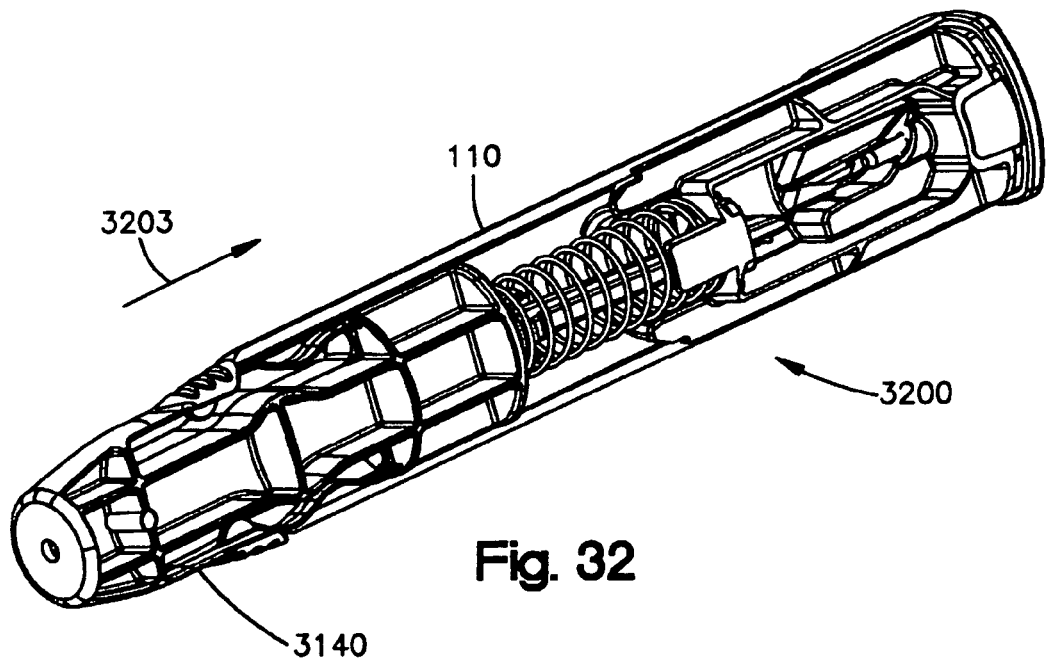
FIG. 32 is a schematic perspective view of an auto-injector trainer with the non-locking needle cover of FIG. 31 according to the invention.

In another embodiment of the invention, auto-injector trainers alternatively have a non-locking needle cover, as shown in FIGS. 30-32. Non-locking needle covers do not lock out when the needle cover is in the extended position. A non-locking needle cover may thus be easier for a user to reset than a needle cover that locks out when in the extended position, because the user would not have to manipulate locking arms 240. FIG. 30 shows one embodiment of a non-locking needle cover 3040. Needle cover 3040 does not have a beveled end surface 244a at juncture 3005 of bend portion 3043 and elongated portion 3044 as does needle cover 140 (which in needle cover 140 is shaped to contact the end surface of outer body 110). FIG. 31 shows another embodiment of a non-locking needle cover 3140, which has no locking arms 240, but instead has outer ribs 3144 that do not prevent needle cover 3140 from retracting back into outer body 110 from the extended position. FIG. 32 shows an auto-injector trainer 3200 with non-locking needle cover 3140 in the extended position. To reset, a user forces needle cover 3140 in the direction of arrow 3203 back into outer body 110.

The process of assembling the trainer 100 will now be described in greater detail in connection with FIGS. 20-22. As shown in FIG. 22(*a*), the needle cover 140 is inserted into the outer body 110 such that the needle cover 140 partially extends from the opposite end 114 of the outer body 110. The spring assembly 150 is inserted into the outer body 110, as shown in FIG. 22(*b*), such that the needle cover arm 145 extends through the center of the spring assembly 150. The spring assembly 150 is oriented within the outer body 110 by engaging the spring guide projections 148.

The trainer actuation assembly 130 is inserted into the outer body 110, as shown in FIG. 22(*c*). The needle cover arm 145 is positioned within the central cavity 330. The guide tooth 146 engages the ramp 333a of the retention detail 333. The guide tooth 146 travels along the ramp 333a such that the arm 145 flexes and the guide tooth 146 and arm 145 clear the retention detail 333. As the assembly 130 is further inserted into the outer body 110, retention details 238a-c on wall 231 are snap fit into the openings 113a, 113b, and 113c on the outer body 110 and the needle arm 145 is directed into race track 331. The needle arm 145 and the guide tooth 146 are directed into race track 331 when the guide tooth 146 contacts the guide detail 332. The guide tooth 146 comes to rest on retention ledge 331a.

Figure 23:
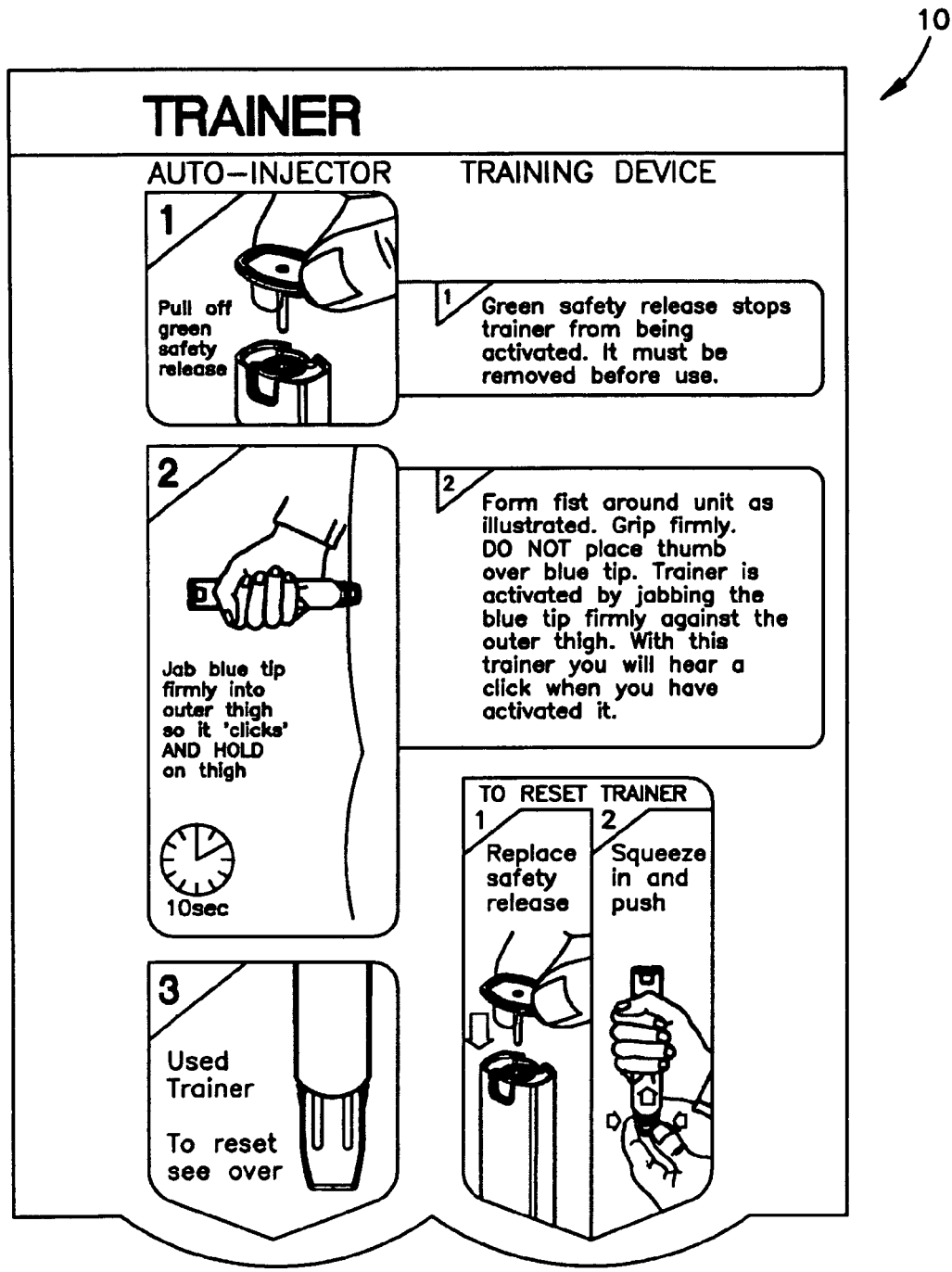
FIG. 23 is a schematic view of a label for use on an auto-injector trainer.

As shown in FIG. 22(*d*), the safety pin 120 is inserted into the trainer actuation assembly 130. The downwardly extending pin 125 of the safety pin 120 is inserted into the retention hole 432 in cavity 330. The pin 125 engages the tooth 146 and arm 145 to prevent the needle cover arm 145 from passing over the activation ledge 331c. As such, the needle cover 140 is retained in a retracted position. The trainer 100 is then in a fully assembled position, as shown in FIG. 22(*e*). The label 10, shown in FIG. 23, is then applied to the outer surface of the outer body 110. The trainer 100 is now ready for operation.

The operation of the trainer 100 will now be described in connection with FIGS. 2(*a-d*), 4(*a-d*), 14, and 23. FIGS. 2(*a*) and 4(*a*) show the trainer 100 in its operative states. To perform a training operation, which simulates the injection operation of an auto-injector, the user removes the safety pin 120, as shown in FIGS. 2(*b*), 4(*b*), and 23. Pin 125 no longer impedes the movement of guide tooth 146 and cover arm 145. The end surface 141 of the needle cover 140 is firmly placed against the thigh (or other surface) of the user, as indicated in the label of FIG. 23. As the needle cover 140 is pressed against the thigh, the guide tooth 146 of the needle cover arm 145 moves away from the retention ledge 331a in race track 331, as shown in FIG. 4(*c*). The cover arm 145 travels along the path indicated by the arrows in FIG. 14. The guide tooth 146 is directed toward the activation ledge 331c through contact with angled faces 331b. An audible click is then generated as the guide tooth 146 drops off activation ledge 331c. The needle cover arm 145 is now positioned on the opposite side of the guide detail 332, as shown in FIG. 4(*c*). The trainer 100 is held against the thigh for a predetermined period of time (e.g., 10 seconds) to simulate the injection operation with an auto-injector.

Figure 4D:
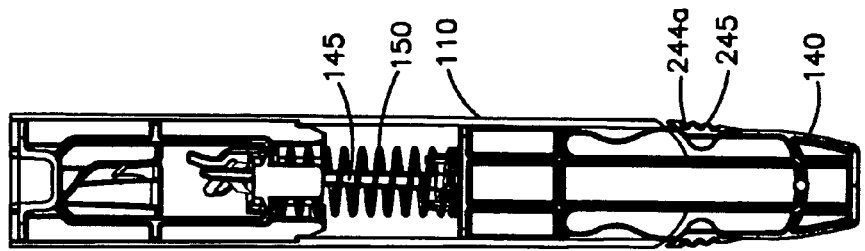
FIGS. 4(a)-4(d) are cross-sectional side views of the auto-injector trainer of FIGS. 2(a)-2(d), respectively, illustrating the operating sequence of the auto-injector trainer.
Figure 4C:
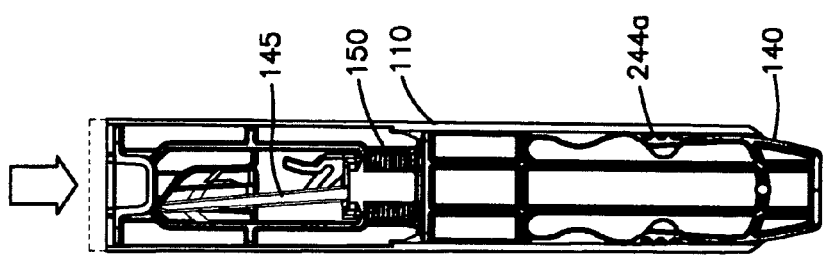
Figure 4B:
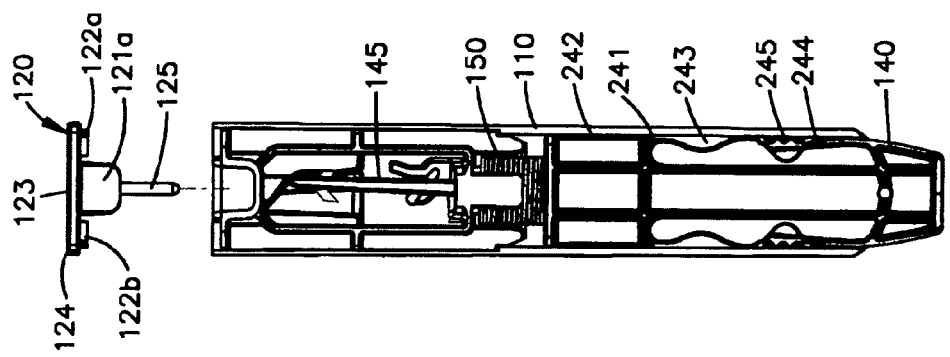
Figure 4A:
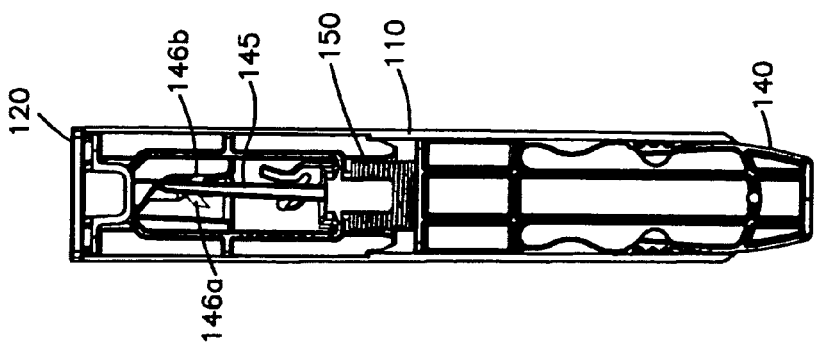
Figure 8:
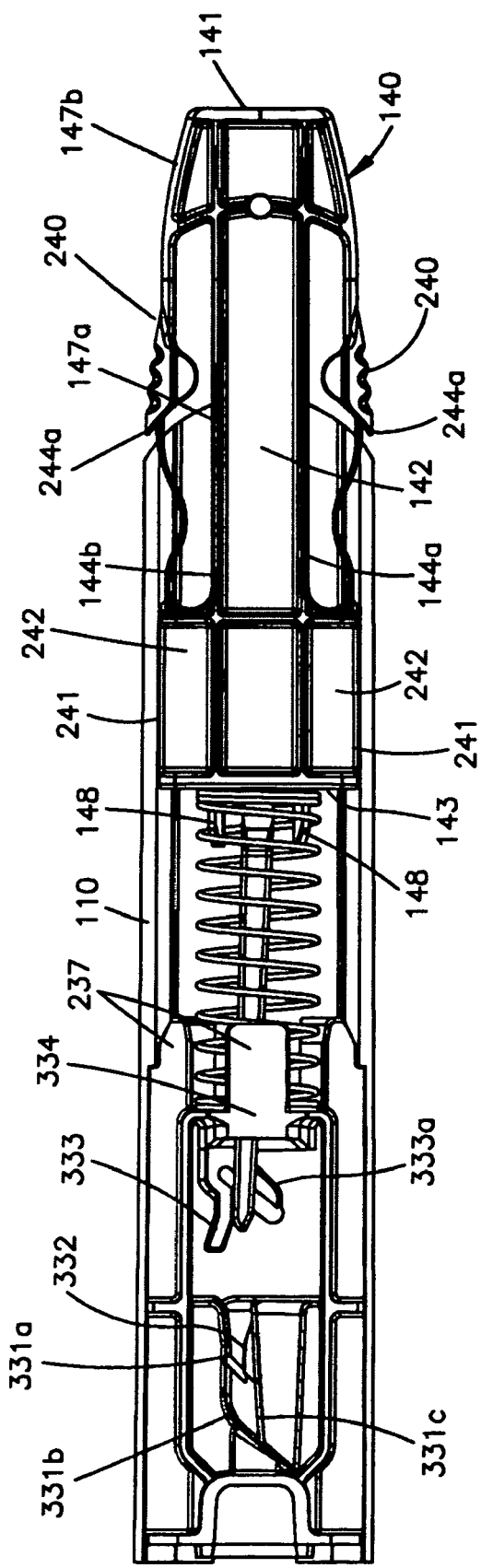
FIG. 8 is a cross-sectional side view of the auto-injector trainer illustrating the position of the needle cover arm within the actuation assembly with the needle cover in an extended position after operation of the trainer.

As the trainer 100 is pulled away from the thigh, the needle cover arm 145 is free to travel in race track 331 in the direction away from hole 432. The bias force of the spring assembly 150 causes the needle cover 140 to be moved in a direction such that the cover 140 extends outward from the outer body 110, as shown in FIGS. 2(d) and 4(d). As the needle cover 140 moves in an outward direction, the outer surface of the enlarged locking portion 244 rides along the inner surface of the outer body 110. When the beveled end surface 244a of the locking portion 244 clears the end of the outer body 110, the force of the bend portion 243 and the compressive force from the compressed locking portion 244 biases the locking portion 244 in an outward direction such that the beveled end surface 244a engages the end surface of the outer body 110 to prevent the cover 140 from being inserted back into the outer body 110. The outward travel of the needle cover 140 is limited by the guide tooth 146 when it is received in retention detail 333, as shown in FIGS. 8 and 20. The guide bridge 334, shown in FIG. 4(d), is positioned such that the guide tooth 146 cannot be lifted out of retention detail 333. The needle cover 140 is now maintained in an extended position, which in FIG. 4(d), corresponds to the arrangement of an auto-injector after use.

Figure 3D:
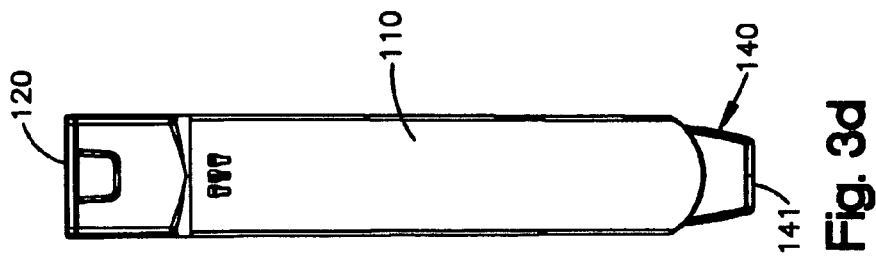
FIGS. 3(a)-3(d) are side views illustrating the operating sequence of resetting the auto-injector trainer for reuse.
Figure 3C:
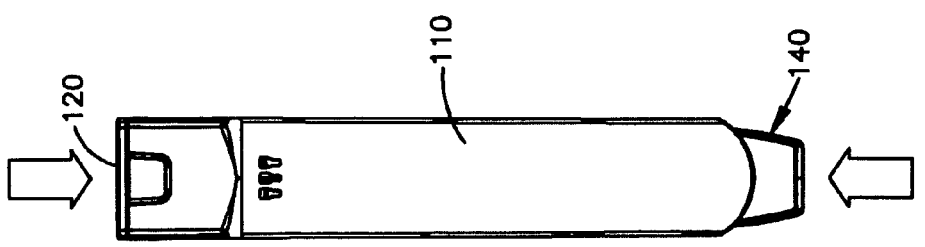
Figure 3B:
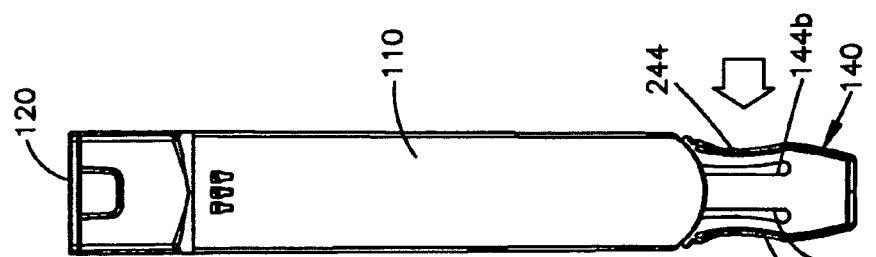
Figure 3A:
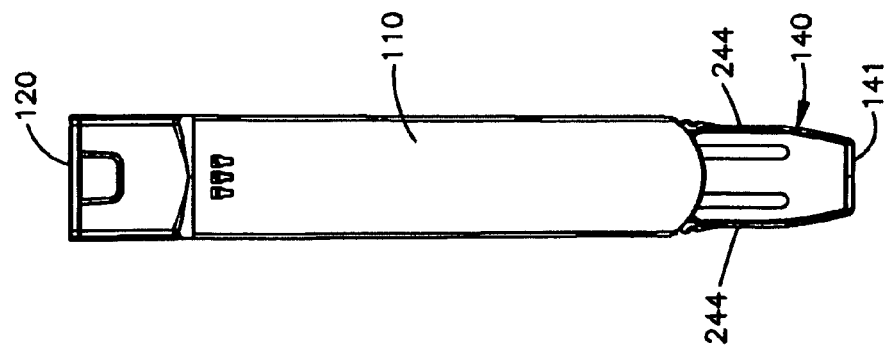

The resetting operation of the trainer 100 will now be described in connection with FIGS. 3, 5, 7, 8, 14, and 20. Prior to resetting, the guide tooth 146 is received in the retention detail 333, as shown in FIGS. 8 and 20. The resetting operation is started by inserting the safety pin 120, FIG. 5(a), such that pin 125 extends through hole 432 into cavity 330, FIG. 5(b), to the position shown in FIG. 3(a). The user applies an inward compressive force to the locking portions 244 such that the locking arms 240 are compressed, as shown in FIG. 3(b). The stop member 245 limits the inward travel of the locking portion 244. Once the bevel edge surface 244a clears the edge of the open end of the outer body 110, the user applies a force (e.g., a finger or hand on the safety pin 120) against the safety pin 120 and then pushes the needle cover 140 back into the outer body 110.

As the cover 140 is pushed, the guide tooth 146 moves out of retention detail 333. The guide detail 332 directs the guide tooth 146 and cover arm 145 along one side of race track 331. When an audible click is heard, the guide tooth 146 has moved past the retention ledge 331a. At this point, if the cover 140 were released, the cover 140 would not move to the extended position under the force of the spring assembly 150 because the guide tooth 146 engaged the retention ledge 331a. The pin 125 limits the travel of the guide tooth 146 within racetrack 331 so that the guide tooth 146 and arm 145 cannot travel over the activation ledge 331c, as shown in FIG. 5(d). The trainer 100 is now in the position shown in FIGS. 3(d) and 5(d) and is now ready for use.

Various modifications and variations to the above-described auto-injector trainer can be made without departing from the scope of the invention.

We claim:

1. A training device for training a user on the operation of an auto-injector that dispenses a medicament, the training device comprising:
   a housing;
   a cover member slidably received within the housing, the cover member slidable from a retracted position relative to the housing prior to operation of the training device to an extended position relative to the housing after operation of the training device;
   a spring member for biasing the cover member into the extended position;
   an actuation assembly operatively connected to the cover member, the actuation assembly controlling the movement of the cover member from the retracted position to the extended position in response to activation of the trainer by the user; and
   a safety pin removably connected to the actuation assembly, the safety pin preventing activation of the training device and movement of the cover member from the retracted position to the extended position when the safety pin is connected to the actuation assembly.

2. The training device of claim 1 wherein the cover member includes an elongated arm having a guide tooth formed thereon, the guide tooth operatively connected to the actuation assembly.

3. The training device of claim 2 wherein the actuation assembly comprises:
   a central cavity; and
   a guide track formed within the cavity, the guide tooth constructed and arranged to travel along the guide track as the cover member moves from a substantially retracted position to the extended position.

4. The training device of claim 3 wherein the actuation assembly further includes a guide adjacent the guide track for orienting the guide tooth within the guide track.

5. The training device of claim 3 wherein the actuation assembly further includes a retention bridge for contacting the elongated arm such that the guide tooth remains positioned within the guide track.

6. The training device of claim 3 wherein the guide track includes a retention ledge formed therein, the retention ledge constructed and arranged to limit movement of the cover member in a first direction such that the cover member does not move from the retracted position to the extended position in the first direction.

7. The training device of claim 6 wherein the guide tooth engages the retention ledge.

8. The training device of claim 6 wherein the safety pin is constructed and arranged to limit the movement of the cover member in a second direction opposite the first direction such that the cover member does not move from the retracted position to the extended position when the safety pin is connected to the actuation assembly.

9. The training device of claim 8 wherein the safety pin engages the guide tooth and the elongated arm to limit movement of the cover member in the second direction.

10. The training device of claim 8 wherein upon removal of the safety pin, the cover member is capable of moving in the second direction in response to an application of force on the cover member.

11. The training device of claim 3 wherein the guide track includes an actuation ledge formed therein, the actuation ledge constructed and arranged such that the cover member travels from the retracted position to the extended position in response to the guide tooth traveling over the actuation ledge.

12. The training device of claim 11 wherein the cover member travels from the retracted position to the extended position under the bias of the spring assembly.

13. The training device of claim 11 wherein the actuation assembly includes a retention assembly to limit further movement of the cover member when the cover member is in the extended position.

14. The training device of claim 13 wherein the actuation assembly further includes a retention bridge for contacting the elongated arm such that the guide tooth remains positioned within the retention assembly.

15. The training device of claim 1 wherein the cover member includes at least one locking assembly to prevent movement of the cover member from the extended position to the retracted position when the cover member is in the extended position.

16. The training device of claim 15 wherein the cover member includes an elongated body and the at least one locking assembly comprises:
a locking arm connected to the elongated body, the locking arm including a locking portion having a locking surface, the locking arm flexing to a locked position such that the locking surface engages a portion of the housing to maintain the cover member in the extended position.

17. The training device of claim 16 wherein the locking arm is constructed and arranged to be temporarily compressed such that the locking surface disengages the housing to enable the cover member to move from the extended position to the retracted position.

18. The training device of claim 17 wherein the locking portion includes a stop to limit the compression of the locking arm.

19. The training device of claim 1 wherein a pin on the safety pin is received within an opening in the actuation assembly to prevent actuation of the trainer.

20. The training device of claim 1 wherein the safety pin includes at least one tab extending therefrom, the at least one tab being compression fit into a complimentary recess formed in the actuation assembly.

21. The training device of claim 1 wherein the safety pin enables a resetting operation of the cover member returning to the retracted position from the extended position when the safety pin is connected to the actuation assembly.

22. The training device of claim 4 wherein the guide is constructed and arranged within the central cavity to direct the guide tooth towards a retention ledge in the guide track during a resetting operation.

23. The training device of claim 3 wherein the safety pin engages the guide tooth and the elongated arm to limit movement of the cover member in a second direction during a resetting operation.

24. A method of using a training device to train a user of an auto-injector to properly operate the auto-injector to dispense a dosage of medicament, the training device including a housing, a cover member slidably received within the housing between a retracted position relative to the housing and an extended position relative to the housing, an actuation assembly operatively connected to the cover member to control the movement of the cover member from the retracted position to the extended position, and a safety pin removably connected to the actuation assembly, the method comprising:
removing the safety pin from one end of the training device to place the training device in an operative state;
operating the training device such that the cover member moves from the retracted position to the extended position, placing the training device in an inoperative state;
replacing the safety pin; and
resetting the training device.

25. The method of claim 24 wherein operating the training device comprises:
pressing an opposite end of the training device against a predetermined surface of the user;
holding the training device against the predetermined surface for a predetermined amount of time; and
removing the training device from the predetermined surface allowing the cover member to move from the retracted position to the extended position.

26. The method of claim 25 wherein removing the training device comprises removing the training device from the predetermined surface allowing the cover member to move from the retracted position to the extended position and allowing the cover member to lock in the extended position via a releasable locking assembly.

27. The method of claim 25 wherein pressing an opposite end of the training device against a predetermined surface includes applying a force on the training device such that the cover member temporarily moves from the retracted position to a further retracted position.

28. The method of claim 27 further comprising generating an audible sound when the cover member moves from the retracted position to the further retracted position.

29. The method of claim 26 further comprising:
releasing the releasable locking assembly; and
applying a force to one end of the cover member to move the cover member from the extended position to the retracted position.

30. The method of claim 29 wherein:
the releasable locking assembly includes a locking arm connected to an elongated body on the cover member;
the locking arm includes a locking portion having a locking surface;
the locking arm flexes to a locked position such that the locking surface engages a portion of the housing to maintain the cover member in the extended position; and
releasing the locking assembly includes applying a compressive force on the locking arm such that the cover member can be inserted into the housing.

* * * * *